US011992692B2

(12) United States Patent
Dascoli et al.

(10) Patent No.: US 11,992,692 B2
(45) Date of Patent: *May 28, 2024

(54) PEDIATRIC AND ADULT DEFIBRILLATOR

(71) Applicant: ZOLL Medical Corporation, Chelmsford, MA (US)

(72) Inventors: Melissa M. Dascoli, Wakefield, MA (US); Charles E. Sawyer, Jr., Sudbury, MA (US); Bill Gastrock, Waltham, MA (US); Dustin Boutet, Somerville, MA (US); Gary A. Freeman, Waltham, MA (US); James Wilson, Norwood, MA (US); Brian Stonecipher, Thousand Oaks, CA (US); Ian Durrant, Acton, MA (US); George Reilly, Chelmsford, MA (US); Mark Bates, West Newton, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 155 days.

This patent is subject to a terminal disclaimer.

(21) Appl. No.: 17/644,155

(22) Filed: Dec. 14, 2021

(65) Prior Publication Data

US 2022/0105352 A1 Apr. 7, 2022

Related U.S. Application Data

(63) Continuation of application No. 16/375,348, filed on Apr. 4, 2019, now Pat. No. 11,298,558, which is a (Continued)

(51) Int. Cl.
*A61N 1/39* (2006.01)
*A61N 1/04* (2006.01)

(52) U.S. Cl.
CPC .......... *A61N 1/3912* (2013.01); *A61N 1/046* (2013.01); *A61N 1/39044* (2017.08);
(Continued)

(58) Field of Classification Search
CPC ..... A61N 1/3993; A61N 1/3904; A61N 1/046
See application file for complete search history.

(56) References Cited

U.S. PATENT DOCUMENTS 6,047,212 A 4/2000 Gliner et al.
6,125,298 A 9/2000 Olson et al.
(Continued)

*Primary Examiner* — Alyssa M Alter
(74) *Attorney, Agent, or Firm* — ZOLL Medical Corporation

(57) ABSTRACT

This document describes an automated external defibrillator comprising a control configured to switch between a pediatric operating mode and an adult operating mode, wherein each operating mode comprises a mode-specific energy configuration and a mode-specific user configuration; an indicator configured to provide an indication of the operating mode in use during a resuscitation process; one or more processors configured to switch to the mode-specific energy configuration and the mode-specific user configuration upon a change of operating mode between the pediatric operating mode and the adult operating mode such that the automated external defibrillator delivers a defibrillating shock to a patient based on the mode-specific energy configuration; and an interface of the automated external defibrillator provides resuscitation instructions to a user based on the mode-specific user configuration.

35 Claims, 17 Drawing Sheets

Related U.S. Application Data continuation of application No. 15/440,501, filed on Feb. 23, 2017, now Pat. No. 10,300,293.

(60) Provisional application No. 62/300,535, filed on Feb. 26, 2016.

(52) U.S. Cl.
CPC ......... *A61N 1/3925* (2013.01); *A61N 1/3987* (2013.01); *A61N 1/3993* (2013.01)

(56) References Cited

U.S. PATENT DOCUMENTS

| | | |
|---|---|---|
| 6,990,373 B2 | 1/2006 | Jayne et al. |
| 7,062,321 B2 | 6/2006 | Lyster et al. |
| D658,297 S | 4/2012 | Powers et al. |
| 9,079,044 B2 | 7/2015 | Powers |
| 10,201,696 B2 | 2/2019 | Freeman et al. |
| 10,300,293 B2 * | 5/2019 | Dascoli ............... A61N 1/39044 |
| 11,298,558 B2 * | 4/2022 | Dascoli ................ A61N 1/3987 |
| 2003/0055459 A1 | 3/2003 | Lyster et al. |
| 2004/0162586 A1 | 8/2004 | Covey et al. |
| 2005/0070964 A1 | 3/2005 | Hansen et al. |
| 2005/0267536 A1 | 12/2005 | Freeman et al. |
| 2014/0243916 A1 | 8/2014 | Freeman et al. |
| 2015/0094625 A1 | 4/2015 | Freeman et al. |
| 2017/0252571 A1 | 9/2017 | Dascoli et al. |
| 2019/0224486 A1 | 7/2019 | Dascoli et al. |

* cited by examiner

PEDIATRIC AND ADULT DEFIBRILLATOR

CROSS-REFERENCE TO RELATED APPLICATIONS

This application is a continuation application of and claims priority under 35 U.S.C. § 120 to U.S. patent application Ser. No. 16/375,348, filed on Apr. 4, 2019, which is a continuation application of and claims priority under 35 U.S.C. § 120 to U.S. patent application Ser. No. 15/440,501, filed Feb. 23, 2017, which claims priority under 35 U.S.C. § 119(e) to U.S. Patent Application Ser. No. 62/300,535, filed on Feb. 26, 2016. The entire contents of each application is hereby incorporated by reference.

TECHNICAL FIELD

This application relates to the field of adult and pediatric defibrillation and defibrillation equipment.

BACKGROUND

Sudden health problems such as sudden cardiac arrest and injuries caused by accidents result in death and/or permanent injury of thousands of people every year. Fast and competent care to resuscitate such victims of these problems can be essential to positive outcomes in such situations. For example, it is said that the chance of surviving a sudden cardiac arrest falls by ten percent for every minute of delay in providing effective treatment.

Resuscitation treatments for patients suffering from cardiac arrest generally include clearing and opening the patient's airway, providing rescue breathing for the patient, and applying chest compressions to provide blood flow to the victim's heart, brain, and other vital organs. If the patient has a shockable heart rhythm (ventricular fibrillation or pulseless ventricular tachycardia), resuscitation also may include defibrillation therapy.

SUMMARY

This document describes an automated external defibrillator having a control configured to switch between a pediatric operating mode and an adult operating mode, wherein each operating mode comprises a mode-specific energy configuration and a mode-specific user configuration; an indicator configured to provide an indication of the operating mode in use during a resuscitation process; one or more processors configured to switch to the mode-specific energy configuration and the mode-specific user configuration upon a change of operating mode between the pediatric operating mode and the adult operating mode such that the automated external defibrillator delivers a defibrillating shock to a patient based on the mode-specific energy configuration; and an interface of the automated external defibrillator provides resuscitation instructions to a user based on the mode-specific user configuration.

In some implementations, the control of the automated external defibrillator is further configured to switch by toggling the operating mode of the automated external defibrillator back and forth between the pediatric operating mode and the adult operating mode. In some implementations, the control is further configured to switch the operating mode when the one or more computer processors determine that the electrode assembly in communication with at least one of the electronic ports is usable in both the pediatric operating mode and the adult operating mode.

In some implementations, the one or more computer processors are configured to determine when the electrode assembly is configured only for the pediatric operating mode, and, in response, the indicator automatically indicates the pediatric operating mode, and the control is disabled. In some implementations, the one or more computer processors are configured to determine when the electrode assembly is configured only for the adult operating mode, and, in response, the indicator automatically indicates the adult operating mode, and the control is disabled. In some implementations, the automated external defibrillator can have a user interface configured to provide at least one of instructions specific to the pediatric operating mode and instructions specific to the adult operating mode. In some implementations, the user interface includes a visual display configured to provide the at least one of instructions specific to the pediatric operating mode and instructions specific to the adult operating mode.

In some implementations, the one or more computer processors are configured to enter the pediatric operating mode and, in response, cause the user interface to provide the instructions specific to the pediatric operating mode. In some implementations, when the automated external defibrillator is in the pediatric operating mode, the user interface is configured to omit chest compression feedback provided to a user. In some implementations, the one or more computer processors are configured to enter the adult operating mode and, in response, cause the user interface to provide the instructions specific to the adult operating mode. In some implementations, the user interface is configured to toggle between the instructions specific to the pediatric operating mode and the instructions specific to the adult operating mode when the control is used to toggle between the modes.

In some implementations, the user interface is configured to toggle between the instructions specific to the pediatric and adult operating modes during administration of one or more steps of resuscitation. In some implementations, the user interface is configured to toggle between the instructions specific to the pediatric and adult operating modes during at least one of placing pads on the patient and administering CPR to the patient. In some implementations, a level of the defibrillating shock is different for the pediatric operating mode and the adult operating mode. In some implementations, changing the operational mode immediately prepares the one or more capacitors for the operating mode in use. In some implementations, when the operational mode is changed the one or more capacitors are discharged.

In some implementations, the control comprises a button. In some implementations, the control comprises the indicator. In some implementations, the indicator comprises at least one of a visual indicator, a lighted display, an audio indicator, a verbal indicator and a haptic indicator. In some implementations, the one or more computer processors are configured to determine at least one of depth and rate of chest compressions based on a motion signal received arising from chest compressions applied to the patient.

In some implementations, when the automated external defibrillator is in the adult operating mode, the one or more computer processors are configured to compare the at least one of depth and rate of chest compressions to a desired range and provide chest compression feedback to a user. In some implementations, the chest compression feedback comprises at least one of visual feedback, audio feedback and haptic feedback.

In some implementations, the automated external defibrillator can have a user interface configured to provide a visual display of numerical values of the determined at least one of depth and rate of chest compressions when the automated external defibrillator is set to a basic life support mode. In some implementations, when the automated external defibrillator is in the adult operating mode, the one or more computer processors are configured to compare the at least one of depth and rate of chest compressions to a desired range and provide chest compression feedback to a user. In some implementations, when the automated external defibrillator is in the pediatric operating mode, the user interface is configured to refrain from providing chest compression feedback to a user.

In some implementations, the one or more computer processors are configured to cause the one or more capacitors to be charged to a voltage that is greater when the operating mode is in the adult operating mode than when the operating mode is in the pediatric operating mode. In some implementations, the one or more computer processors are configured to cause a resistance in a circuit between the one or more capacitors and the patient to be greater when the operating mode is in the pediatric operating mode than when the operating mode is in the adult operating mode. In some implementations, the one or more processors are configured to analyze one or more portions of the ECG signal, wherein the analysis differs between the pediatric operating mode and the adult operating mode.

In some implementations, the automated external defibrillator can have one or more capacitors for delivering a defibrillating shock to a patient; one or more electronic ports configured to receive signals indicative of sensed physiological parameters of the patient, and to communicate the defibrillating shock to the patient based on a signal produced from an analysis of the sensed physiological parameters of the patient; a control for toggling an operating mode of the automated external defibrillator back and forth between a pediatric operating mode and an adult operating mode during a resuscitation process; and an indicator configured to provide an indication of the current operating mode in use; and one or more computer processors configured to determine if an electrode assembly in communication with at least one of the electronic ports is usable in at least one or both of the pediatric operating mode and the adult operating mode.

In some implementations, the one or more computer processors are configured to adjust an energy output of the defibrillating shock based on whether the operating mode is in the pediatric operating mode or the adult operating mode. In some implementations, the control is configured to change the operating mode when the one or more computer processors determine that the electrode assembly in communication with at least one of the electronic ports is usable in both the pediatric operating mode and the adult operating mode. In some implementations, the one or more computer processors are configured to determine when the electrode assembly is configured only for the pediatric operating mode, and, in response, the indicator automatically indicates the pediatric operating mode, and the control is disabled. In some implementations, the one or more computer processors are configured to determine when the electrode assembly is configured only for the adult operating mode, and, in response, the indicator automatically indicates the adult operating mode, and the control is disabled. In some implementations, the automated external defibrillator can have a user interface configured to provide at least one of instructions specific to the pediatric operating mode and instructions specific to the adult operating mode. In some implementations, the user interface includes a visual display configured to provide the at least one of instructions specific to the pediatric operating mode and instructions specific to the adult operating mode.

In some implementations, the one or more computer processors are configured to enter the pediatric operating mode and, in response, cause the user interface to provide the instructions specific to the pediatric operating mode. In some implementations, when the automated external defibrillator is in the pediatric operating mode, the user interface is configured to omit chest compression feedback provided to a user. In some implementations, the one or more computer processors are configured to enter the adult operating mode and, in response, cause the user interface to provide the instructions specific to the adult operating mode. In some implementations, the user interface is configured to toggle between the instructions specific to the pediatric and adult operating modes during administration of one or more steps of resuscitation. In some implementations, the one or more computer processors are configured to cause the one or more capacitors to be charged to a voltage that is greater when the operating mode is in the adult operating mode than when the operating mode is in the pediatric operating mode. In some implementations, the one or more computer processors are configured to cause a resistance in a circuit between the one or more capacitors and the patient to be greater when the operating mode is in the pediatric operating mode than when the operating mode is in the adult operating mode.

The techniques described herein may have one or more of the following advantages. The AED operating mode can be toggled during operation such that it is operating in a mode that is appropriate for treating a particular patient. The AED can change the treatment given to the patient depending on the operating mode of the AED. The operating mode can be changed quickly during treatment. The operating mode of the AED can be clear to the user. The AED can be used to treat adult patients and pediatric patients. The AED can display one or more instructions that are appropriate for the patient being treated, such as displaying instructions for treating a pediatric patient when a pediatric patient is being treated and displaying instructions for treating an adult patient when an adult patient is being treated. The AED can change the feedback to the user depending on the skill level of the user.

DESCRIPTION OF THE FIGURES

FIGS. 2B-13 show examples of instructions provided by an AED.

DETAILED DESCRIPTION

Figure 1A:
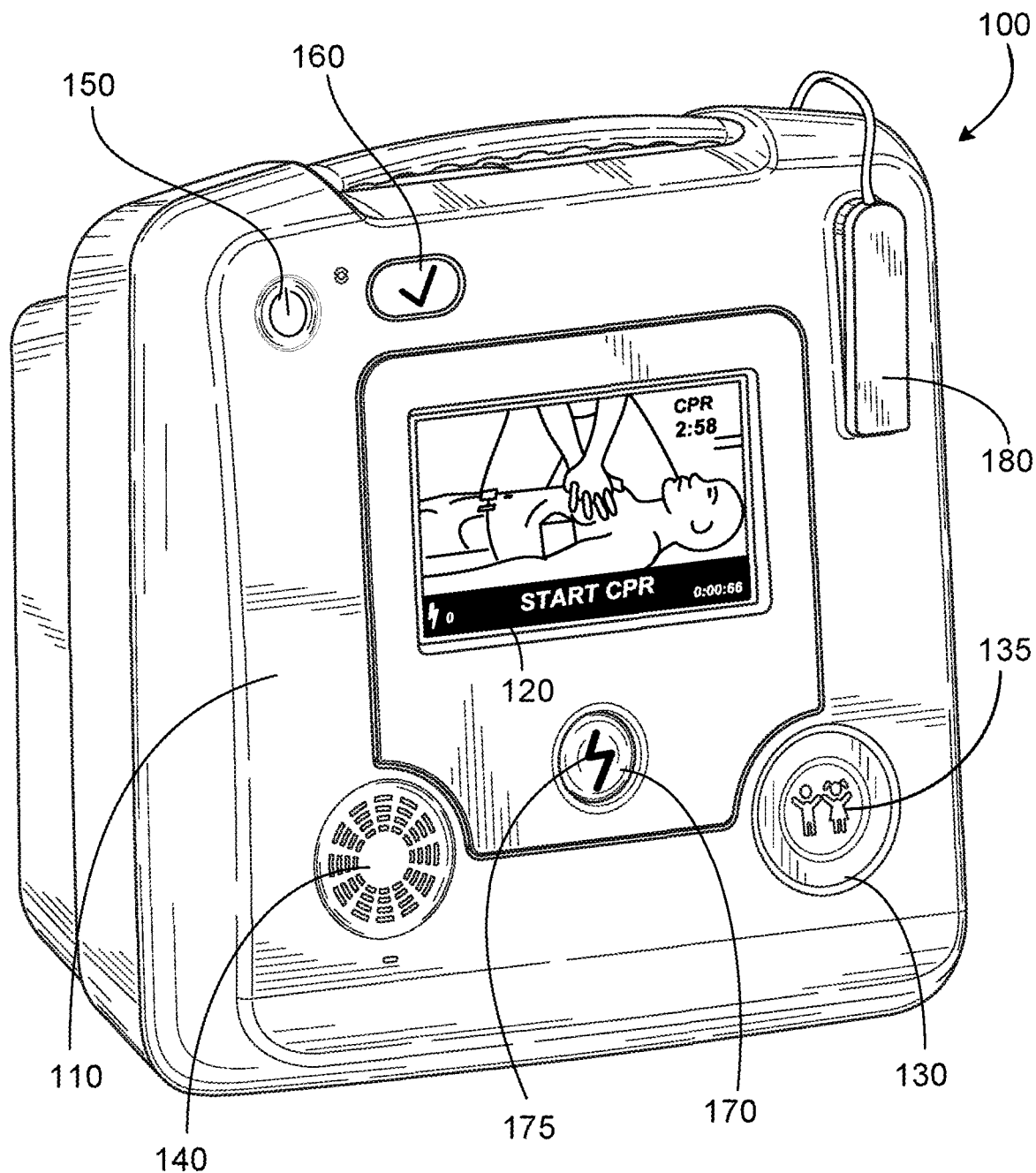
FIG. 1A shows an example of an AED.

Adult and pediatric patients often require different treatments during defibrillation therapy. As one example, the defibrillating shock for an adult or relatively large sized individual characteristic of an adult will involve a greater amount of energy (e.g., could be approximately 100 Joules greater) than that for a child or comparatively smaller person. As provided herein, the term AED refers generically to any device or system that is able to provide a defibrillation shock to patients as appropriate for resuscitative treatment.

An automated external defibrillator (AED) may have numerous settings which can adjust the device to accommodate both adult and pediatric patients. In some cases, the procedure for treating the different kinds of patients (e.g. adult and pediatric patients) can vary. A user, who might be using the AED for the first time in an emergency situation, may not be aware of the difference in treating different kinds of patients. Hence, the present disclosure provides for a defibrillation apparatus (e.g., AED, defibrillator/monitor, etc.) that is configured to operate in pre-configurable modes, for example modes suitable for either adult or pediatric resuscitation. Such an apparatus may include a control that is able to cause the apparatus to dynamically toggle between adult and pediatric operating mode during resuscitation, as well as provide a prominent indication as to which mode the apparatus is currently in. While in a particular mode of operation (e.g., adult, pediatric), the manner in which the apparatus communicates and/or guides the rescuer through the resuscitative process may differ appropriately.

An AED can provide different mode-specific user configurations for treating different kinds of patients. For example, the user configuration of the AED may be mode-specific to whether the AED is set to an adult operating mode or a pediatric operating mode. If the AED is operating in an adult operating mode, the AED can provide instructions as well as treatment settings for treating an adult. If the AED is operating in a pediatric operating mode, the AED can provide instructions as well as treatment settings for treating a pediatric patient (e.g. a child). As another example of differences in user configurations depending upon modes of operation, if the user is an experienced user or professional responder, the AED can provide instructions which can be more suitable for the user, for example, by operating alternatively in either an advanced or basic mode.

In some cases the AED can automatically detect the kind of patient to which resuscitative treatment is to be applied, for example, by electrode detection, amongst others. The AED may detect the type of electrode connected thereto by any suitable manner, such as for example, via detecting a particular resistor ID associated with the type of electrode. In other cases, the user can select the desired operating mode and the AED will operate according to the selected mode. Such operation of the AED can help to ensure that preferred instructions for treatment can be given to users who may be in position to treat either adult or pediatric patients.

FIG. 1A shows an example of an Automated External Defibrillator (AED) 100 capable of operating in a pediatric operating mode and an adult operating mode. The AED 100 has a chassis 110 which houses and protects the internal components of the AED 100. The chassis 110 is constructed to provide one or more inputs and outputs, which may include a user interface. The user interface includes a graphical display 120 which can display instructions, treatment feedback, and other information to a user which may be useful for administering resuscitative therapy.

As will be described in more detail below, the user interface of the AED 100 has a control 130 for changing the operating mode of the AED 100. In some implementations, the control 130 can switch the operating mode between an adult operating mode and a pediatric operating mode. In some embodiments, the control provides the ability for the AED to switch between adult and pediatric operating modes dynamically during the resuscitation process. The resuscitation process may include various activities performed and/or treatments delivered to a patient during the course of resuscitation (e.g. determining the patient's state of consciousness, contacting a local emergency number, placing electrodes on the patient, analyzing the patient's ECG, detecting a shockable rhythm, delivering a defibrillation shock, performing CPR, etc.). For example, as the rescuer begins resuscitative therapy, the AED may be set to adult operating mode by default, however, it might not be until further into the resuscitation process that the rescuer recognizes that the AED should be switched to the pediatric operating mode. Accordingly, the rescuer may switch the AED setting from adult operating mode to pediatric operating mode at any time during the resuscitation process and the AED will be able to instantly accommodate the switch and seamlessly continue instructions for the resuscitative process.

The AED 100 has an indicator 135 for providing to the user an indication (e.g., illumination, audible sound, display, etc.) of the current operating mode in use. The AED 100 includes a speaker 140. The speaker 140 can provide auditory instructions and/or other feedback to a user during treatment. The AED 100 includes a switch 150 for turning the AED 100 into an on or off state. The AED 100 can include a readiness indicator 160 which reports whether the AED 100 needs maintenance or other repair such that it is unfit for current use. The AED 100 can include a control, such as a button or switch, for activating treatment, such as a defibrillating shock. In FIG. 1, for example, the control is a shock button 170. The AED 100 includes a port 180. The port 180 can receive signals from sensors, for example, regarding one or more physiological parameters of the patient. Such physiological parameters (e.g., ECG signal) may be analyzed by the processor according to an appropriate algorithm to make a determination of whether a defibrillating shock should be administered to the patient. The port 180 can communicate signals such as a defibrillating shock. For example, a cable leading to defibrillating electrodes can be interfaced with the port 180.

The AED 100 includes several internal components that enable the AED to be used for defibrillation of multiple kinds of patients. The AED includes a computer processor (described in further detail below with respect to FIG. 14). Among other things, the computer processor can be configured to determine in which operating mode the AED should be delivering treatment.

The computer processor can be configured to determine whether adult electrodes are connected to the port 180 and subsequently ensure that the operating mode of the AED is in the adult operating mode. For instance, if adult-specific electrodes (e.g., CPR-D-Padz®, CPR Stat-Padz®, Stat-Padz® provided by ZOLL Medical Corp.) are connected to the AED, the processor may sense that adult-specific electrodes are being employed and deactivate the control 130 that would otherwise allow a user to switch the AED from adult operating mode to pediatric operating mode. Similarly, if the AED is set to pediatric operating mode and adult-specific electrodes are connected to the AED, the processor may then automatically switch the AED to adult operating mode.

The computer processor may also be configured to determine whether pediatric electrodes are connected to the port 180 and subsequently change the operating mode to the pediatric operating mode. For instance, if pediatric-specific electrodes (e.g., Pedi-Padz® provided by ZOLL Medical Corp.) are connected to the AED, the processor may determine that pediatric-specific electrodes are being employed and automatically switch the AED from adult operating mode to pediatric operating mode. The processor may also deactivate the control 130 so that a user is unable to switch the AED from pediatric operating mode to adult operating mode as long as the pediatric-specific electrodes are connected thereto. When the pediatric-specific electrodes are connected, the processor may also transmit a signal so that the indicator 135 provides an indication to the user that the AED is in pediatric operating mode.

The computer processor may be configured to determine whether the electrode assembly connected to the port 180 is capable of both pediatric and adult treatment (e.g., Uni-Padz® provided by ZOLL Medical Corp.) and enable the operating mode to be changed using the control 130. In such instances, when the electrode assembly configured for both adult and pediatric treatment is connected to the AED, the process may recognize this capability and allow the control 130 to toggle between adult and pediatric operating mode at any point during resuscitation. This process is described in greater detail below.

Other than the computer processor, the internal components of the AED may include one or more capacitors. The capacitors can be charged during use of the AED. The capacitors can be quickly discharged though an external electrode assembly, interfaced with the AED via the port 180, to provide a therapeutic electric shock. The capacitors can discharge in such a way as to correctly deliver an appropriate electric shock having a desired level of energy (e.g., pre-configuration default set to 120-200 J for an adult patient, 50-85 J for a pediatric patient) to the patient during treatment. The capacitors can provide electric shock to the patient at different levels of intensity/energy. The levels of intensity/energy can be controlled by the computer processor. In some embodiments, the energy configuration of the AED may change between adult and pediatric modes, for example, by changing the energy level of the defibrillation shock, by controlling the average current delivered during the defibrillation shock, etc. Accordingly, the energy configuration of the AED may be mode-specific, depending on whether the AED is in the adult operating mode or the pediatric operating mode. The level of defibrillation shock energy is based on the amount of stored charge provided to the capacitors via a charging current or voltage. For example, when storing charge for a defibrillating shock, a greater amount of charge may be stored within the capacitor(s) when the AED is set to adult operating mode as compared to when the AED is set to pediatric operating mode. In additional examples, once the capacitor(s) are sufficiently charged, the stored charge is at least partially dissipated (e.g., by the presence of resistors and/or other dissipating element(s) located between the capacitor(s) and the defibrillating electrode(s)), so as to reach the desired level of defibrillation shock energy. For example, a greater resistance may be provided upon discharge when the AED is set to pediatric operating mode as compared to when the AED is set to adult operating mode, to reduce the total energy delivered during a therapeutic shock than would otherwise be the case. In some examples, the user can configure the defibrillation shock energy. In some examples, as discussed herein, the defibrillation shock energy can be determined by the operating mode of the AED. In additional examples, the defibrillation current delivered to the patient may be controlled during shock delivery to deliver a current sufficient for defibrillating a pediatric patient versus that sufficient to defibrillate an adult patient.

In addition to changing the energy configuration of the AED between an adult and pediatric operating mode, the analysis configuration may also be different in the two different mode. That is, the AED may exhibit mode-specific analysis configurations, depending whether the AED is in an adult operating mode or a pediatric operating mode. For example, in the pediatric operating mode a shock analysis algorithm specific for pediatric patients may be used. The pediatric shock analysis algorithm can be calibrated to analyze a child's ECG signal rather than an adult's EGC signal such that the AED can make a more accurate determination of whether a shock should be delivered to the pediatric patient. The AED can measure the ECG baseline content, QRS rate, width and variability, amplitude, and temporal regularity and determine whether a shockable rhythm exists. For the pediatric patient, one or more of the measured values can be different for a shockable rhythm than for the adult patient. As another example, in the pediatric operating mode, analysis of data from chest compression sensors and/or ventilation sensors may be adapted for pediatric patients.

Each operating mode of the AED 100 can include various configurations of the AED for delivering treatment. The configuration(s) can include hardware settings, software settings, characteristics of treatment, selection of instructions to be delivered to the user, or any other setting which changes functionality of the AED. In some examples, the operating mode of the AED can be the configuration which optimizes the AED to deliver treatment to a particular type of patient. Types of patients can include, for example, adult patients and pediatric patients. The AED can be optimized in a number of ways. For example, the user configuration parameters can be changed between the pediatric and adult operating modes such that the instructions on the display 120 are adjusted for each stage of treatment to be relevant to the pediatric patient when the AED is operating in pediatric operating mode, or relevant to the adult patient when the AED is operating in the adult operating mode. In one example the adult operating mode can be set to the default user configuration, which can be modified for a pediatric patient when the pediatric operating mode is enabled.

In some examples, the level of the electric shock delivered can be changed. Examples of the differences in treatment for adult patients and pediatric patients are further described below and in relation to FIGS. 3-13.

In addition to adult and pediatric operating modes, which can be examples of clinical modes related to treatment of a patient, the AED can operation in other non-clinical modes and sub-modes which are related non-treatment functionality such as configuration or diagnostics. For example, the AED can operate in a battery mode, a basic configuration mode (e.g., intended for basic life support personnel), and an advanced configuration mode (e.g., intended for advanced life support personnel). The battery mode may be a mode where the AED tests a new battery inserted into the AED. The AED can operate in a fully-automatic mode wherein the AED automatically delivers shock therapy treatment to a patient without waiting for input from the user to deliver the shock. The AED can operate in a semi-automatic mode wherein the AED waits for user input to deliver the shock, such as the press of a button, before the AED delivers shock therapy treatment to a patient. Other sub-modes can include one or more professional modes (e.g., for basic or advanced life support personnel) and a non-professional mode (e.g. a lay-person mode). In various embodiments, when operating in one or more of the professional modes (e.g., basic life support mode), for example, the AED can display different information to the user who is presumed to be a more sophisticated user than a typical user. For example, the professional mode include more feedback regarding the quality of CPR administered to the patient and fewer instructions than in the non-professional mode. In some examples, the AED can initialize to either a professional mode or non-professional mode by default, depending on pre-configured user settings. For instance, the user may desire to configure the AED to initialize in professional mode for various reasons, such as location of the AED (e.g., close proximity to basic life support professionals) and/or the intended user of the particular AED. In some examples, the professional mode can be called a basic life support mode. In some examples, the professional mode is a sub-mode of the adult or pediatric operating modes, such that when the AED is in adult operating mode, the AED can operate in a professional mode or non-professional mode. In some examples, when the AED is in pediatric operating mode, the AED can operate in a professional mode or non-professional mode.

Various resuscitative treatments can include, for example, any stage required for the defibrillation or care of a patient using the AED, such as initializing the AED, preparing the electrode assembly for use, affixing the electrode assembly to the patient, measuring vitals of the patient, applying an electric shock, performance and analysis of CPR, and so on. Examples of various stages of treatment are described in further detail below with respect to FIGS. 3-13.

The chassis 110 of the AED houses and protects the internal components of the AED. The corners of the AED can be rounded, truncated, beveled or otherwise structured so that the chassis 110 is free of sharp edges and, hence, may be easy and safe for a person to handle. A handle can be attached to the chassis 110 for the AED to be comfortably and conveniently carried. Various input and output components of the AED can be flush with the chassis exterior such that the exterior has a smooth and sleek feel/appearance. For example, in FIG. 1, the control 130, speaker 140, and power button 150 are seated in the chassis exterior such that they do not protrude outward from the chassis exterior but rather form depressed features relative to the outer casing surface of the chassis.

The chassis can be constructed from any suitable material, such as a plastic or other rigid material. The chassis colors can be chosen such that a colorblind user can distinguish labels marking the AED 100 as such from the chassis. The chassis colors can be chosen to soothe the user and avoid colors which may induce stress in the user, such as bright red characteristic of warning signs and labels. The chassis colors can be chosen such that the AED can be recognizable and distinguishable from other medical devices, which tend to be white, black, and gray. For example, the chassis can be green-yellow and the label can be blue.

The AED may have a user interface which includes a display 120. The display 120 can be a full-color screen, such as a LED-backlit screen. The display 120 can be covered by a touch-sensitive film or other device such that the display 120 has touch-screen functionality. The display 120 can be used to show instructions for treatment, warnings, a status of the AED, or other information which can be relevant to treatment of the patient. In some examples, the display 120 can show still images of instructions for treatment. In some examples, the display 120 can show animated instructions for treatment. In some implementations, the display 120 can show real-time or near real-time feedback, measurements, or both based on signals provided from the electrode assembly or other sensors or inputs of the AED.

As noted above, the AED has a control 130 which can be used to change the operating mode, e.g., pediatric operating mode or adult operating mode. The control 130 can be easily manipulated by the user to change the operating mode of the AED during use of the AED. In some examples, the control can be used to change the operating mode of the AED at any time during use of the AED and/or during the resuscitation process. For example, the control 130 can be a button. When the button is depressed by the user, the AED changes its operating mode. For example, the button can dynamically toggle the AED between an adult operating mode and a pediatric operating mode. In some implementations, if the electrodes are only capable of one kind of operating mode then the button can be disabled from changing the operating mode. Other controls may be possible, for example, the control may be provided as a switch, touch screen activation and/or other suitable method.

As described above, the indicator 135 may provide an indication to the user as to the current mode of operation of the AED 100. The indicator can include any method of signaling to the user what the current mode of operation is such that the user can perceive the mode of operation at any time during treatment. The indicator 135 can be such that if the user approaches a scene of treatment after treatment has already begun, the user can immediately (e.g., with little to no delay) determine in which mode of operation the AED is currently operating. For instance, as shown, the indicator can be located on the control 130 and/or can be a part of the control 130. In FIG. 1, for example, the indicator is provided as a pediatric symbol 135 and is located directly on the control 130. When the button is depressed during use of the AED, the indicator 135 illuminates to show that the AED is operating in the pediatric operating mode. The indicator 135 is illuminated whenever the AED 100 is operating in pediatric operating mode. The indicator 135 remains free of illumination whenever the AED is operating in the adult operating mode. In this example, since there are two modes of operation, the illumination of the indicator 135 or the lack of illumination of the indicator 135 is an immediate indication of the operation mode currently in use. Some examples of indicators can include a visual indicator such as illumination of the pediatric symbol as depicted in FIG. 2, an audio indicator such as a tone from the speaker 140, a lighted display such as the display 120, a verbal indicator such as a verbal instruction from the speaker 140, a haptic indicator such as a dial, switch, or other haptic indicator, and/or any other suitable manner of indication.

As discussed, each mode of operation for the AED can be different from other modes of operation. A mode of operation can have one or more of a mode-specific series of instructions (e.g. instruction to a user for different stages of treatment), prompts, display images, and treatment measurements, which are described in more detail below. Each mode of operation may have a treatment regimen which is appropriate for a particular class of patient. For example, the AED can have an adult operating mode of operation which is used for adult patients. In some examples, the AED has a pediatric operating mode of operation which is used for pediatric patients.

The adult operating mode of operation is used for treatment of adult patients and may include a user configuration adapted for the resuscitation of adult patients. For example, the AED display 120 may provide instructions and feedback information which is suitable for treatment of the adult patient. As described in more detail below in regard to FIGS. 3-13, during the adult operating mode of operation, the display shows instructions for treatment of the adult patient with the AED. For example, the display shows instructions for preparing the adult patient for treatment, placing the electrode assembly on the adult patient, performing CPR on the adult patient, shocking the adult patient when appropriate, and any other stages of treatment as well as relevant feedback from the electrode assembly for each of these stages.

The pediatric operating mode of operation is used for treatment of pediatric patients and may include a user configuration adapted for the resuscitation of pediatric patients. For example, the AED display 120 may provide instructions and feedback information which is suitable for treatment of pediatric patient. As described in more detail below in regard to FIGS. 3-13, during the pediatric operating mode of operation, the display shows instructions for treatment of the pediatric patient with the AED. For example, the display shows instructions for preparing the pediatric patient for treatment, placing the electrode assembly on the pediatric patient, performing CPR on the pediatric patient, and shocking the pediatric patient when appropriate, as well as relevant feedback from the electrode assembly for each of these stages.

In addition to having a mode-specific series of images on the display 120 for each mode of operation, the AED performs treatment which is suitable for a particular patient. For example, when operating in the adult operating mode, the AED performs treatment which is suitable for an adult patient but might not be suitable for a pediatric patient. For example, the level of electric shock set by the AED can be higher for treatment of an adult patient than the level of electric shock set by the AED for treatment of a pediatric patient. The AED system may be configured to provide escalating rectilinear biphasic defibrillation energies in varying amounts depending on whether the AED is set to the adult operating mode or the pediatric operating mode. For example, when set to adult operating mode, in the clinical configuration, the respective defibrillation energies provided by the AED may be 120 J for the first defibrillation shock, 150 J for the second defibrillation shock and 200 J for the third defibrillation shock; and, when set to pediatric operating mode, the respective defibrillation energies provided by the AED may be 50 J for the first defibrillation shock, 70 J for the second defibrillation shock and 85 J for the third defibrillation shock. In various embodiments, for adult or pediatric operating modes, defibrillation energies provided by the AED may be set according to pre-configured defaults or may be set by a user via configuration of the AED during a non-clinical mode. For example, the user may configure the AED to deliver therapeutic shocks at energy levels other than those noted above, for the adult operating mode and/or pediatric operating mode.

The system may be configured to apply a defibrillating shock according to a rectilinear biphasic waveform, such as those administered by defibrillators provided by ZOLL Medical Corp. Depending on the mode to which the AED is set (e.g., adult operating mode, pediatric operating mode), and how the defibrillation(s) may be escalated (e.g., first, second, third shock) the rectilinear biphasic waveform may be administered so as to exhibit an appropriate level of therapeutic energy to the patient. Illustrative examples of electrotherapy circuits that may be suitable for administering a rectilinear biphasic waveform in accordance with the present disclosure are described in U.S. Pat. No. 5,733,310, entitled "Electrotherapy circuit and method for producing therapeutic discharge waveform immediately following sensing pulse," and is incorporated by reference herein.

Figure 1B:
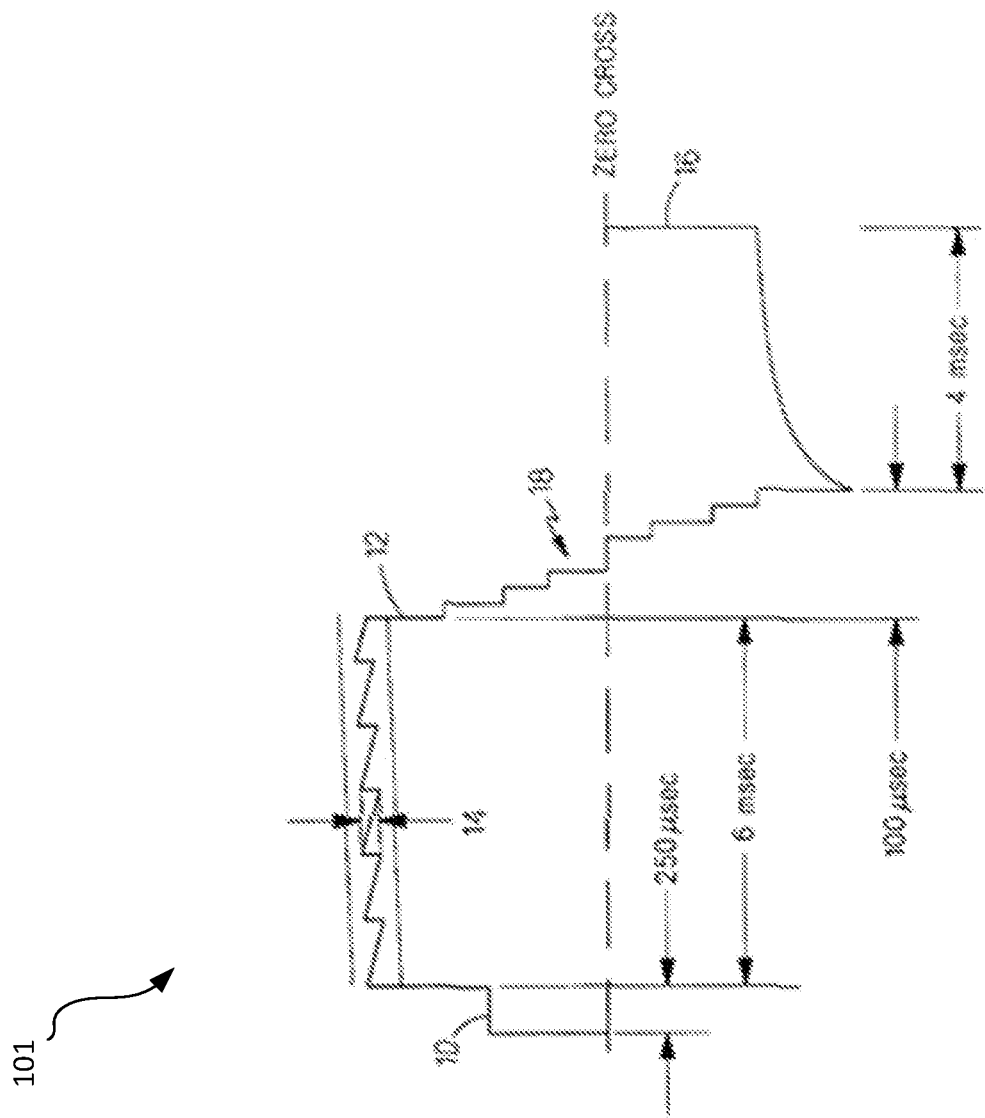
FIG. 1B shows an example of a current waveform.

In certain embodiments in accordance with the present disclosure, as shown in FIG. 1B, a biphasic current waveform 101 may include an initial sensing pulse 10, which has an energy lower than that for administering a therapeutic defibrillating shock. The sensing pulse may allow for the system to compensate for variations in patient impedance, so that an appropriate and consistent amount of energy is delivered to the patient. During the initial sensing pulse, the amount of current flowing through the patient may be measured for the system to calculate patient impedance, according to methods known in the art. It can be appreciated that such a sensing pulse may be optional, for example, the patient impedance may be determined significantly prior to discharge of the biphasic waveform, rather than immediately beforehand. The total resistance during discharge of the defibrillating shock may be adjusted, so that the total impedance of the system and patient remains relatively constant. The sensing pulse is followed by a biphasic defibrillation waveform having energy sufficient for defibrillating the patient's heart. As shown, the biphasic defibrillation waveform may include a substantially rectilinear (linear waveform) positive phase 12 having a sawtooth ripple 14, which is in turn followed by a negative phase 16 that exhibits an exponential decay until the waveform is truncated. The positive phase may optionally include a portion that decreases through a series of steps 18 through the zero crossing up until the beginning of negative phase.

Figure 1C:
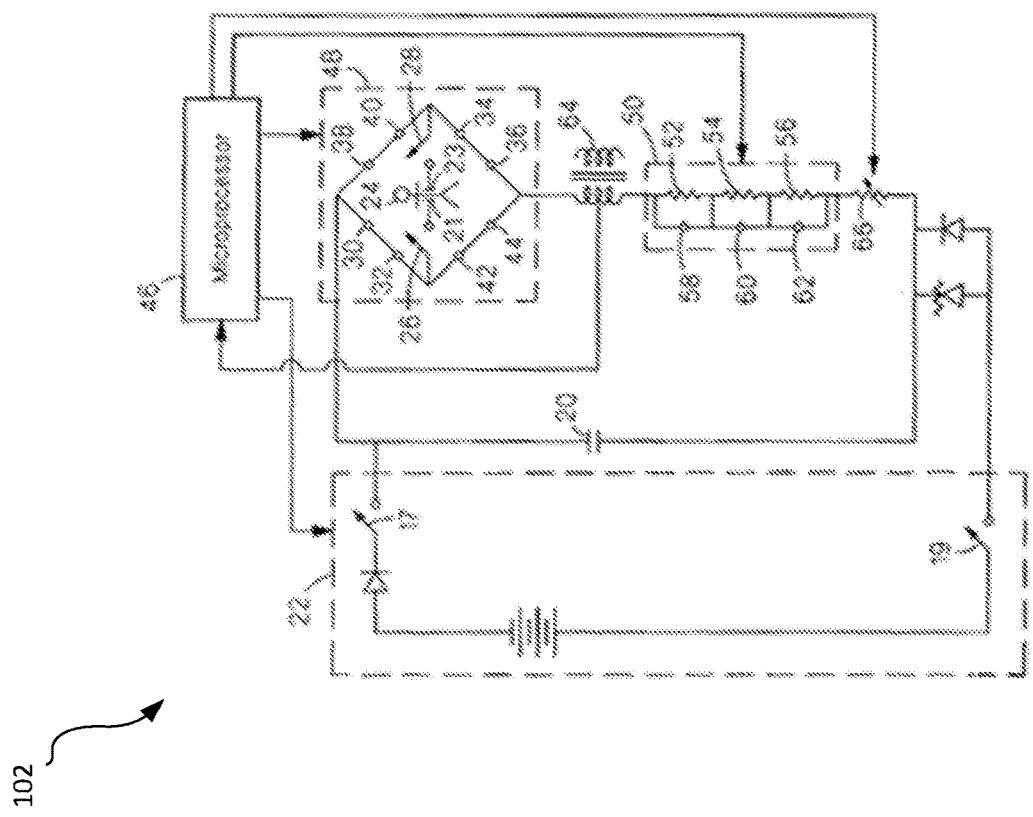
FIG. 1C shows an example of circuitry.

FIG. 1C shows an illustrative embodiment of basic circuitry 102 for producing a suitable biphasic waveform. A storage capacitor 20 (e.g., a single capacitor or multiple capacitors connected in series and/or parallel) may be charged to a maximum voltage according to the mode (e.g., pediatric, adult) set by the AED by a charging circuit 22 while relays 26 and 28 and the H-bridge are open. The electric charge stored in the storage capacitor 20 may be allowed to pass through electrodes 21 and 23 and the body of a patient. Here, relay switches 17 and 19 are opened, and relay switches 26 and 28 are closed. Then, electronic switches 30, 32, 34, and 36 of H-bridge 48 are closed to allow the electric current to pass through the patient's body in one direction, after which electronic H-bridge switches 30, 32, 34, and 36 are opened and H-bridge switches 38, 40, 42, and 44 are closed to allow the electric current to pass through the patient's body in the opposite direction. Electronic switches 30-44 may be controlled by signals provided from a microprocessor 46. Relay switches 26 and 28, which are also controlled by microprocessor 46, may isolate patient 24 from leakage currents of bridge switches 30-44.

Electrodes 21 and 23 may be defibrillation electrodes suitable for administering therapy to an adult and/or pediatric patient, having surfaces for placement on the chest of the patient. A resistive circuit 50 that includes series-connected resistors 52, 54, and 56 may be provided in the current path, each of the resistors being connected in parallel with a shorting switch 58, 60, and 62 controlled by microprocessor 46. The resistors may exhibit different values of resistance and any appropriate number of resistors may be employed. During the initial sensing pulse, when H-bridge switches 30, 32, 34, and 36 are closed, the resistor-shorting switches 58, 60, and 62 are in an open state so that the current passes through each of the resistors in series. Current-sensing transformer 64 senses the current passing through the patient 24, from which microprocessor 46 determines the resistance of the patient 24. In various embodiments, rather than including a current-sensing transformer such as that discussed above, the system may include another component for sensing the current, such as a current-sensing resistor (or other such electrical component) located on either side of the resistor bank.

The initial sensing pulse may be followed by a biphasic defibrillation waveform, without re-charging of the storage capacitor 20 between the initial sensing pulse and the biphasic defibrillation waveform. In this embodiment, if the patient resistance sensed during the initial sensing pulse is low, the resistor-shorting switches 58, 60, and 62 are left open at the end of the sensing pulse so that the resistors 52, 54, and 56 remain in the current path (the resistors are then successively shorted out during the positive phase of the biphasic defibrillation waveform in the manner described below in order to approximate a rectilinear positive phase). The current at the beginning of the positive first phase 12 of the biphasic defibrillation waveform may be the same as the current during sensing pulse 10. If the patient resistance sensed during the sensing pulse is high, some or all of the resistor-shorting switches 58, 60, and 62 are closed at the end of the sensing pulse, thereby shorting out some or all of the resistors. This leads to an upward jump in current at the end of the sensing pulse. Hence, after the sensing pulse, the biphasic defibrillation waveform has an initial discharge current that is controlled by microprocessor 46 based on the patient impedance sensed by current-sensing transformer 64.

By appropriately selecting the number of resistors that remain in the current path, microprocessor 46 reduces (but does not eliminate) the dependence of peak discharge current on patient impedance, for a given amount of charge stored by the charge storage device. Such a configuration provides for the appropriate amount of energy (based on the mode to which the AED is set) to be discharged to the patient. For example, for a patient resistance of 15 ohms, the peak current may be about 25 amps, whereas for a patient resistance of 125 ohms the peak current is about 12.5 amps. (a typical adult patient impedance is about 75 ohms, whereas a pediatric patient impedance may be less).

During the positive phase of the biphasic waveform some or all of the resistors 52, 54, and 56 that remain in series with the patient 24 are successively shorted out. When one of the resistors is shorted out, the current jumps, resulting in a sawtooth ripple waveform. The ripple may have a tendency to be greater in magnitude at the end of the rectilinear phase because the time constant of decay (RC) is shorter at the end of the phase than at the beginning of the phase. If all of the resistors have already been shorted out immediately after the end of the sensing pulse, the positive phase of the biphasic waveform decays exponentially until the waveform switches to the negative phase.

As is shown in FIG. 1B, at the end of the positive phase, the current waveform 101 decreases through a series of rapid steps from the end of the positive phase to the beginning of negative phase, one of the steps being at the zero crossing. Microprocessor 46 accomplishes this by 1) successively increasing the resistance of resistive circuit 50 in fixed increments through manipulation of resistor-shorting switches 58, 60, and 62, then 2) opening the switches in the H-bridge 48 to bring the current waveform down to the zero crossing, then 3) reversing the polarity of the current waveform by closing the H-bridge switches that had previously been open in the positive phase of the current waveform, and then 4) successively decreasing the resistance of resistance circuit 50 in fixed increments through manipulation of resistor-shorting switches 58, 60, and 62 until the resistance of resistance circuit 50 is the same as it was at the end of the positive phase.

A variable resistor 66 may be provided with the other resistors 52, 54, and 56 to reduce the sawtooth ripple. Every time one of the fixed-value resistors 52, 54, or 56 is shorted out, the resistance of variable resistor 66 may automatically increase to a higher value and then decrease until the next fixed-value resistor is shorted out. This tends, to some extent, to smooth out the height of the sawtooth ripple, and reduces the need for smaller increments of the fixed-value resistors (i.e., it reduces the need for additional fixed-value resistor stages).

The switches in the left-hand side of H-bridge 48 can be tested by closing switches 17 and 19, opening switches 26 and 28, closing switches 30 and 32, then after a short time closing switches 42 and 44, then after a short time opening switches 30 and 32, and then after a short time opening switches 42 and 44. If the switches are working properly, current-sensing transformer 64 will sense the passage of current when all four switches are closed, and will sense no current when switches 30 and 32 or switches 42 and 44 are open. Otherwise, current-sensing transformer 64 will detect the possible presence of a short circuit or an open circuit. Similarly, the switches in the right-hand side of H-bridge 48 can be tested by closing switches 38 and 40, then after a short time closing switches 34 and 36, then after a short time opening switches 38 and 40, and then after a short time opening switches 34 and 36. This safety test does not require current to pass through the patient, due to the placement of current-sensing transformer 64 outside the legs of H-bridge 48.

Figure 1D:
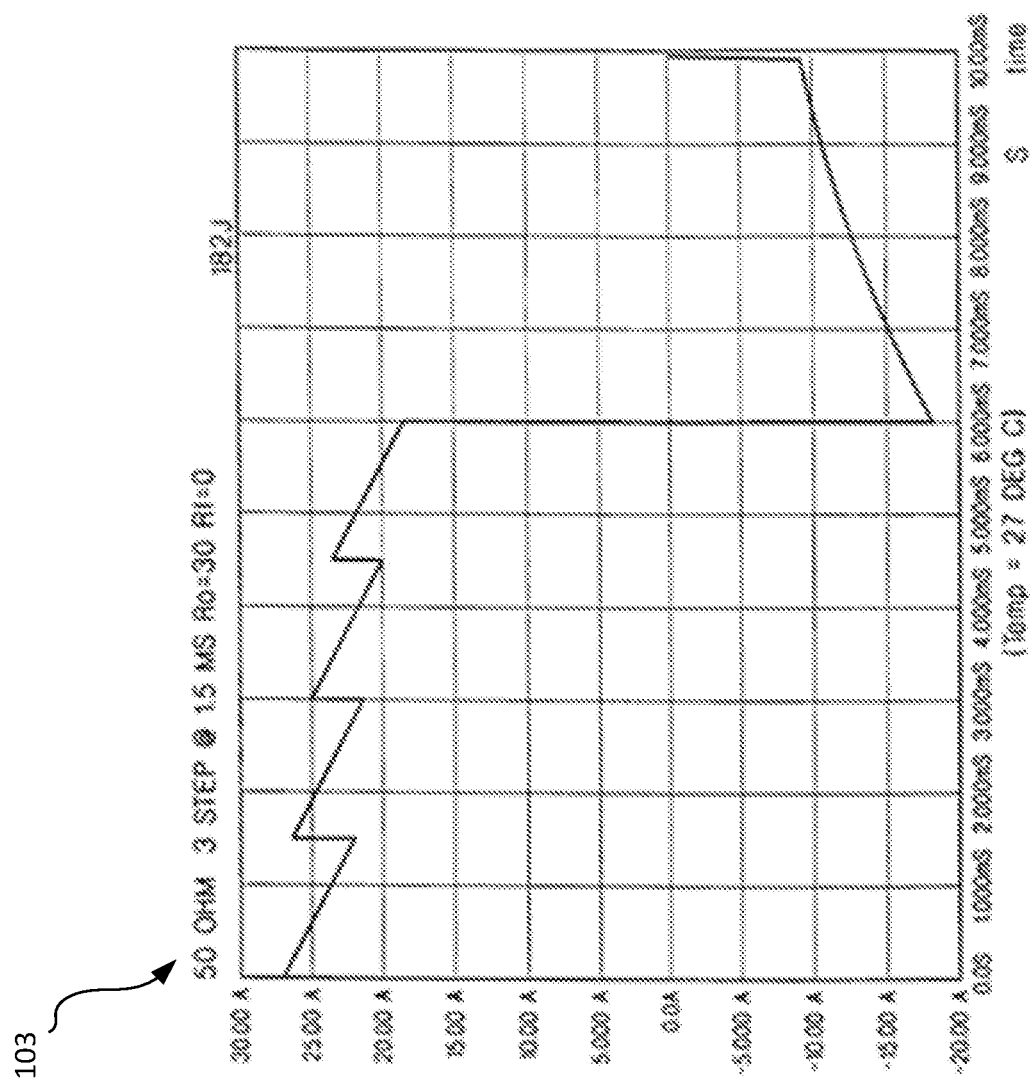
FIGS. 1D-1F show examples of a waveform.

FIG. 1D depicts an example of a rectilinear biphasic waveform 103 based on a patient impedance of 50 ohms. Here, the microprocessor selects an initial series-connected resistance of 30 ohms and a residual series-connected resistance of 0 ohms at the end of the positive phase of the waveform.

A rectilinear biphasic waveform may be delivered according to different energy configurations, depending upon whether an adult or pediatric operating mode is enabled. For example, the table below provides characteristics of a rectilinear biphasic waveform when discharged from the defibrillator at an energy setting of 200 J, an energy setting that may be implemented in an adult operating mode, into patient impedances of 25 ohms, 50 ohms, 100 ohms and 125 ohms, respectively. For a given patient impedance, the first (positive) phase and the second (negative) phase of the waveform may each exhibit a suitable maximum initial current, average current and duration. For example, for an energy setting of approximately 200 J, depending on the measured patient impedance, the maximum initial current during the first and/or second phase may be between approximately 10 A and approximately 35 A, and the average current during the first and/or second phase may be between approximately 10 A and approximately 30 A.

|  | Discharged into 25 ohm load | Discharged into 50 ohm load | Discharged into 100 ohm load | Discharged into 125 ohm load |
| --- | --- | --- | --- | --- |
| First Phase Maximum Initial Current | 32 A | 26 A | 21 A | 17 A |
| First Phase Average Current | 28 A | 22 A | 16 A | 13 A |
| First Phase Duration | 6 ms | 6 ms | 6 ms | 6 ms |
| Interphase duration between first and second phases | 150 μsec | 150 μsec | 150 μsec | 150 μsec |
| Second Phase Maximum Initial Current | 33 A | 19 A | 12 A | 11 A |

|  | Discharged into 25 ohm load | Discharged into 50 ohm load | Discharged into 100 ohm load | Discharged into 125 ohm load |
| --- | --- | --- | --- | --- |
| Second Phase Average Current | 21 A | 14 A | 11 A | 10 A |
| Second Phase Duration | 4 ms | 4 ms | 4 ms | 4 ms |

It can be appreciated that other current levels may be possible for this and other energy settings. The current levels may be adjusted by any suitable method, for example, via a schedule of resistors as discussed above. The duration of the first phase may be about 6 milliseconds, the duration of the second phase may be about 4 milliseconds, and the duration in between phases (interphase) may be about 150 microseconds. It may be possible for the first phase, second phase and the time between phases to last for other durations of time, as appropriate.

Figure 1E:
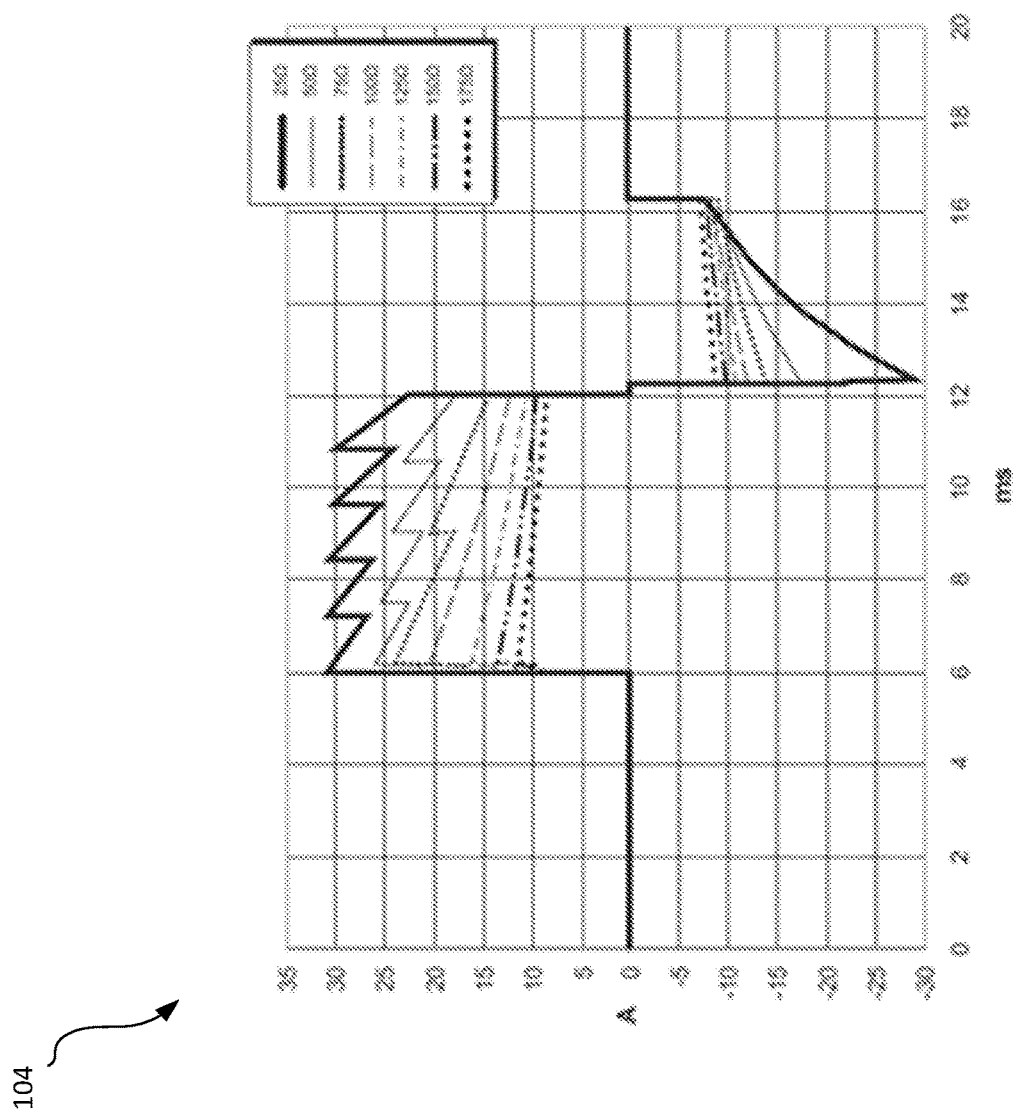

FIG. 1E depicts a graph 104 for an embodiment of a defibrillator that shows a number of rectilinear biphasic waveforms for a defibrillation discharge at an energy setting of 200 J, for patient impedances of 25 ohms, 50 ohms, 75 ohms, 100 ohms, 125 ohms, 150 ohms and 175 ohms. In some embodiments, the energy setting of 200 J may correspond to one or more shocks to be provided when the defibrillator is set to an adult operating mode configuration. Accordingly, the initial charge and/or schedule of resistors may be adjusted to suit the energy setting. The ripple behavior of the first (positive) phase of the waveform may be due to resistors that are employed according to a suitable schedule, each of the resistors exhibiting a suitable level of resistance. For example, for a patient impedance of 25 ohms, the sequence of resistance may be approximately 50 ohms, 40 ohms, 30 ohms, 20 ohms and 10 ohms during the first phase; and for the second phase, the resistance may be approximately 10 ohms.

Figure 1F:
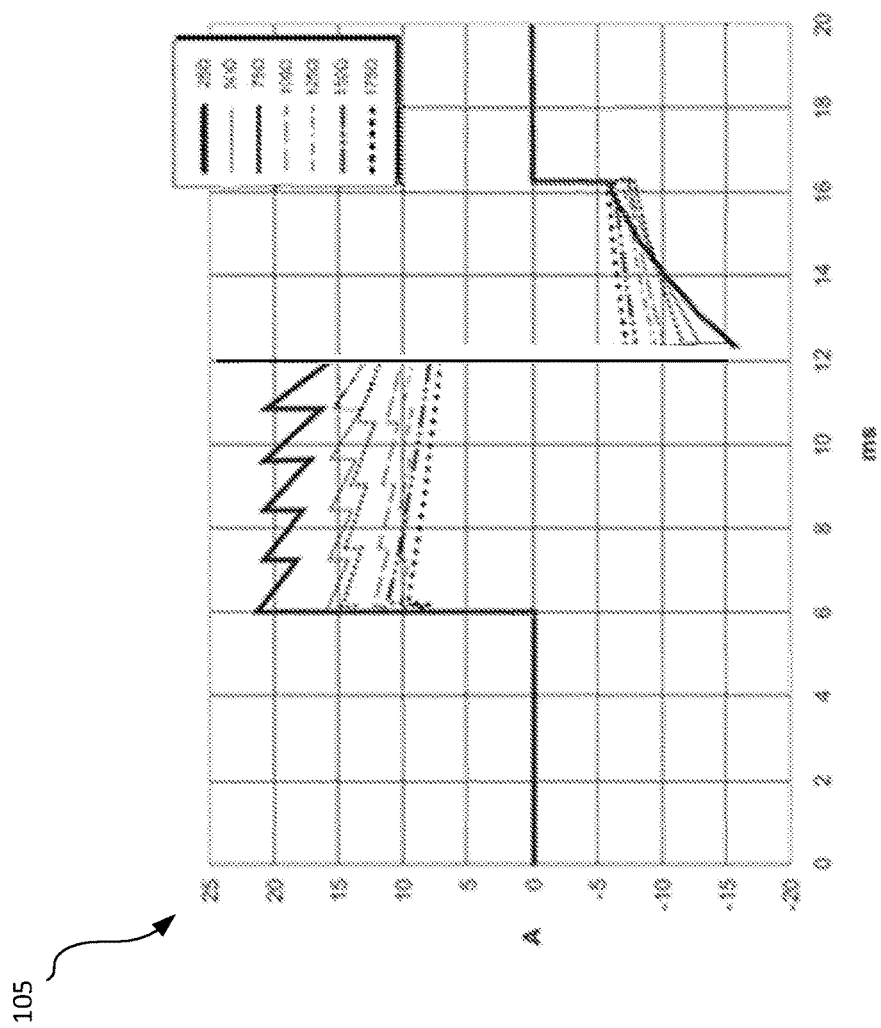

In a pediatric operating mode the energy setting and resistor schedules may be optimized for a pediatric patient. For example, FIG. 1F provides a graph 105 for a defibrillator showing rectilinear biphasic waveforms for a defibrillation discharge at an energy setting of 85 J, for patient impedances of 25 ohms, 50 ohms, 75 ohms, 100 ohms, 125 ohms, 150 ohms and 175 ohms. In certain embodiments, the energy setting of 85 J may correspond to shocks provided when the defibrillator is set to a pediatric operating mode configuration, which is comparatively less than the energy setting for the adult operating mode. Similar to that discussed above for the 200 J setting, the energy setting may set the level of initial charge and/or schedule of resistors, except resulting in a comparatively lower overall current.

In additional examples changing the mode of the defibrillator may change other configurations. For example, the AED 100 might provide CPR feedback that requires a range of chest compression depth for the adult patient that is different from the corresponding range of chest compression depth for the pediatric patient. For example, because adult patients are larger in size than pediatric patients, the recommended chest compression depth for an adult may be greater than the recommended chest compression depth for a child. Configurations specific to analysis of the compression parameters and/or configurations providing instructions to the user may be changed between the modes to be specific to either adult or pediatric patients.

In other implementations the user configurations could be adapted to be different between modes, e.g., when treating a pediatric patient it may be desirable to limit prompting to aid in delivering chest compressions at a recommended rate, e.g. by prompts cuing the timing of chest compressions only, while disabling prompting related to measuring the depth of compression (which may be more erroneous in pediatric patients).

The control 130 of the AED 100 can be used to toggle the operating mode of the AED 100 at any time during treatment. For example, when the button 130 is pressed, the operating mode of the AED 100 is immediately toggled (e.g. with little or no delay perceptible to the user) from one mode to another. The indicator 135 then immediately indicates the new current operating mode. For example, if the operating mode is the adult operating mode and the button 130 is pressed, the operating mode immediately toggles to the pediatric operating mode and the indicator 135 is illuminated. In some examples, if the operating mode is the pediatric operating mode and the button 130 is pressed, the operating mode immediately toggles to the adult operating mode and the indicator 135 turns off. The display 120 can also immediately toggle between adult and pediatric instructions and images when the control 130 is toggled. In some embodiments, the display 120 may further provide an indication of the current mode of the AED (e.g., whether the AED is in adult or pediatric operating mode, or in BLS or non-BLS mode).

When the operating mode is toggled, the AED 100 can immediately prepare itself to operate in the desired mode. In one example, the user may wish to toggle the operating mode from the adult operating mode to the pediatric operating mode after the capacitors are charged and ready to deliver a shock at the level appropriate for treatment of the adult patient. If the user toggles the operating mode to the pediatric operating mode at this stage of treatment, the AED can discharge the capacitors without delivering a shock to the patient and recharge the capacitors to a level appropriate for treating the pediatric patient as quickly as possible for the electronics to safely do so. Conversely, if the user toggles the operating mode from the pediatric operating mode to the adult operating mode after the capacitors are charged and ready to deliver a shock appropriate for treatment of an adult patient, the AED can quickly discharge the capacitors without delivering a shock to the patient and recharge the capacitors to a level appropriate for treating the adult patient. Alternatively, when the AED is already charged for pediatric shock delivery and the user toggles the AED from the pediatric operating mode to adult operating mode, the AED may simply increase the level of charge in the capacitor without having to first discharge and then charge again. Similarly, if the AED is already charged for adult shock delivery and the user toggles the AED from the adult operating mode to pediatric operating mode, the AED may be configured to decrease the level of charge in the capacitor to the appropriate level without having to discharge and then charge again. In some examples, when the operating mode of the AED is toggled at a time when the AED is ready to deliver a shock, the AED 100 can repeat analysis of the patient to ensure that the electric shock is still appropriate for treatment. Since the operating mode of the AED is able to be changed at any stage of treatment, the user can ensure that the AED is in the appropriate operating mode for the patient. For example, if the user accidentally toggles the operating mode during treatment, the user can immediately toggle the operating mode back to the appropriate operating mode without losing a significant amount of time.

The user interface of the AED 100 may include a speaker 140. The speaker 140 can provide audio instructions and feedback to the user during treatment. The speaker 140 can provide audio of the instructions which are displayed on the screen so that the user does not have to read the display. For example, audio instructions such as "wait," "remove shirt," "apply shock," and "start CPR" can be provided at the appropriate stages of treatment. In some examples, the speaker can provide a metronome during CPR. The metronome can assist the user in performing chest compressions by providing pacing sounds to the user during CPR. In some examples, audio feedback can be provided to the user during treatment.

The AED 100 includes a power button 150 and a readiness indicator 160. The power button can be any control which is used to toggle the AED between an on state and an off state. For example, the power button 150 can be a button, switch, dial, or similar. The readiness indicator 160 indicates the condition of the AED. For example, the readiness indicator 160 can indicate whether the AED is ready to provide treatment or whether maintenance is needed. For example, in FIG. 1, the readiness indicator 160 displays a check mark when the AED has performed a self-test and is ready for use. When the AED is not ready for use, the readiness indicator 160 is left blank. For example, the AED may be unfit for use when the battery is low, the capacitors are damaged, fails a self-test, or any other defect exists which can impact performance or safety of the AED. If the readiness indicator 160 does not indicate that the AED is ready for use, the user should not use the AED.

The AED includes a shock button 170. The shock button 170 can be used to apply an electric shock therapy to the patient during treatment. The same shock button 170 can be used for both the adult operational mode and the pediatric operational mode. The shock button 170 can have a shock symbol 175 which indicates that the button is for applying the shock to the patient. For example, the shock symbol 175 can be a lightning bolt. The shock button 170 can be a different color from the rest of the AED. In one example, the shock button 170 can be the different color, such as orange, so that it stands out from the rest of the AED, including the other buttons, and is recognizable when depicted on the display 120, such as depicted in FIG. 2B. In some examples, the shock button 170 can be a different size than other controls such that it is discernable from the other buttons on the AED. In some examples, the shock button 170 can illuminate when the computer processor determines that shock therapy is recommended. In some examples, the shock button 170 can flash when shock therapy is recommended. For instance, when shock is recommended, the shock button 170 may be illuminated or otherwise configured to draw the attention of a rescuer until it is pressed so that a shock is discharged. Once the shock is applied, the shock button 170 may then be dimmed or turned off. The use of the shock button is described in further detail below.

The AED has a port 180. The port 180 can be used to interface the AED with the electrode assembly or other external sensors which can be used with the AED. The port 180 can include both inputs and outputs of the AED. Inputs to the AED can include, for example, ECG waveforms, accelerometer data from a chest compression sensor, impedance information, or other sensor information while treating the patient. Outputs can include, for example, electrical discharge from the capacitors and other control signals to the electrode assembly or interfaced sensors.

The computer processor of the AED can use the inputs to determine the state of the patient and the state of the treatment. For example, the computer processor can detect when the cable is unplugged and subsequently have the AED prompt the user to plug the cable back into the port 180 to continue treatment. In some examples, the computer processor can detect whether electric shock therapy is needed during treatment by analyzing the ECG of the patient. In some examples, the computer processor can read, interpret, and send for display measurements of a rate and a depth of compressions performed by the user. In some examples, the computer processor can detect whether the electrodes of the electrode assembly are suitably affixed to the patient such that the shock therapy can be properly administered to the patient. For example, if one or more of the electrodes of the electrode assembly are improperly attached, the computer processor of the AED can determine that the pads need to be properly affixed to the patient before the shock therapy can be administered to the patient. In some examples, the computer processor can interpret the electrical impedance measured by the electrodes to make such a determination. The AED can subsequently prompt the user to properly affix the pads to the user for treatment as described in greater detail in regard to FIGS. 5-6 below.

The computer processor can use the inputs to determine which operating mode the AED should operate in for treatment. In one example, if an electrode assembly which can operate in both adult and pediatric operating modes is plugged into the port 180, the computer processor can configure the AED to toggle between the adult and pediatric operating modes when the control 130 is toggled. In some examples, if the computer processor detects that an electrode assembly which is plugged into the port 180 is configured only for pediatric or adult use, the computer processor can configure the AED to enter the appropriate operating mode (e.g. adult or pediatric operating mode, respectively). In this example, the indicator 135 indicates the current operating mode, such as illuminating for the pediatric operating mode, but the control 130 is disabled so that the AED remains in the operating mode which is compatible with the attached electrode assembly even when the control 130 is toggled. Such control by the computer processor can assist the user in treating the patient. For example, the user could be confused as to the whether the attached electrode assembly is configured to treat adult patients, pediatric patients, or both, and the computer processor can ensure that the AED operates only in the operating modes with which the electrode assembly is compatible.

Figure 2A:
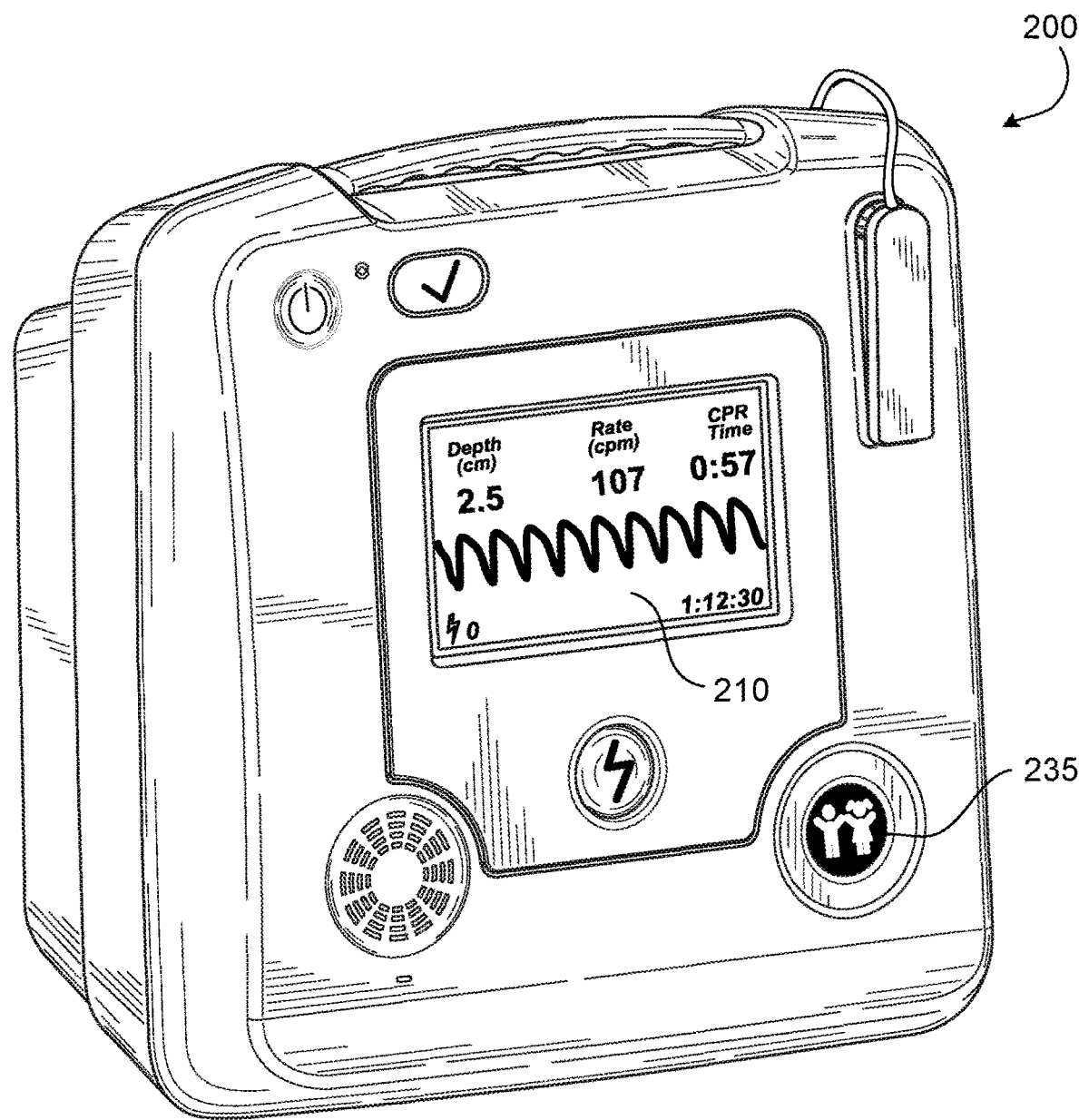
FIG. 2A shows an example of an AED.
Figure 2B:
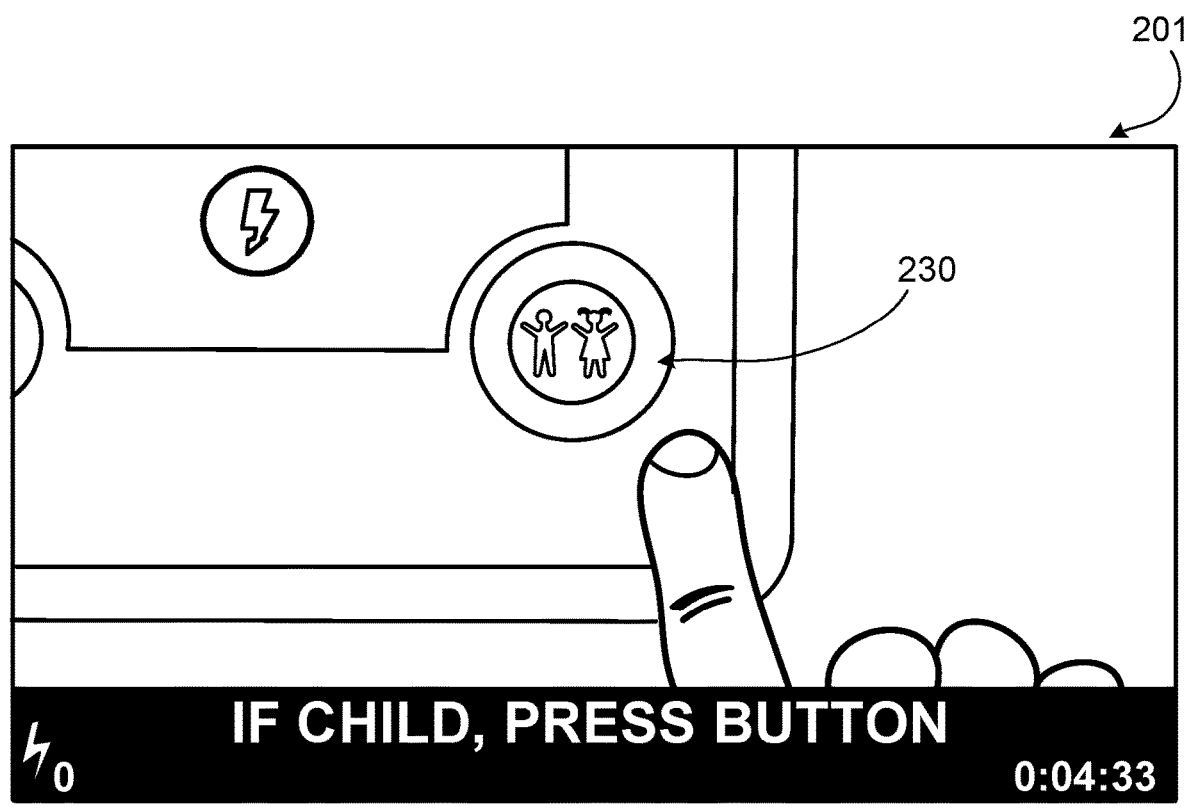

FIG. 2A shows an example of an AED 200 in pediatric operating mode. The indicator 235 is illuminated. The display 210 shows an example ECG waveform from the pediatric patient.

As described above, each operating mode of the AED can include one or more stages of treatment during a resuscitation process. The stages of treatment can include any step taken before, during, or after defibrillation or CPR administration of the patient which are related to the use of the AED. In some examples, the stages of treatment can include one or more of an initialization stage, a configuration stage, an operating mode confirmation stage, a patient preparation stage, an electrode placement stage, a CPR therapy stage, a shock therapy stage, and a treatment conclusion stage. The stages of treatment are discussed in more detail with respect to FIGS. 2B-13.

FIG. 2B shows an example operating mode confirmation instruction 201. The instruction 201 can be displayed on the display 210 during the operating mode confirmation stage. The instruction 201 can include one or more of pictorial instructions, textual instructions, and auditory instructions.

During the operating mode confirmation stage, if the patient is a pediatric patient, the user can be prompted to toggle the control 230 if the patient is a pediatric patient. The default state of the AED 100 can be configured appropriately. For example, the AED may be configured such that the default mode is the mode which may be the most likely mode to be used for a particular AED. For example, if the AED is located in a school or pediatric ward of a hospital, the default mode can be configured to be the pediatric operating mode. In many cases, the AED may be configured so that the default mode is the adult operating mode. As discussed above, if the computer processor detects that the electrode assembly only supports a particular operating mode, the computer processor can automatically configure the AED to operate in the particular operating mode and the operating mode confirmation stage can be skipped. Although the user is instructed to toggle the control during the operating mode confirmation stage, the user can toggle the operating mode by using the control 230 during any stage and can toggle any number of times between modes. In some examples, the user can also operate the AED without toggling the control 230.

The instruction 201 can include textual instructions on the display 120 during the operating mode confirmation stage. The textual instructions can include "if child, press button," "if patient is a child, press child button," "adult patient selected," "child patient selected," or similar.

The instruction 201 can include auditory instructions produced from the speaker 140 during the operating mode confirmation stage. Audio instructions may be provided as an alternative, or in addition, to visual or textual instructions. The textual instructions can include "if child, press button," "if patient is a child, press child button," "adult patient selected," "child patient selected," or similar.

As discussed herein, the AED may have mode-specific user configurations, depending on whether the AED is in an adult operating mode and a pediatric operating mode. During treatment of a patient, the AED can display a mode-specific series of instructions on the display 120. The operating mode can determine the specific user configuration, which includes mode-specific series of instructions are displayed at each stage of treatment. For example, when the operating mode of the AED is the adult operating mode, the mode-specific series of instructions for adult patients is displayed. In some examples, when the operating mode of the AED is the pediatric operating mode, the mode-specific series of instructions for the pediatric patient can be displayed. In various embodiments, the mode-specific series of instructions can be displayed by showing one stage at a time on the display 120. The instruction which is appropriate for the current stage of treatment can be shown. When the next stage of treatment is reached, the next instruction in the mode-specific series of instructions can be displayed. Although, it can be appreciated that instructions for multiple stages of the treatment process may also be shown, displayed, or otherwise provided.

The instructions for treatment can be displayed using pictorial representations. In some examples, the pictorial representations can include pictures or images of what the treatment should look like for the current stage. The pictorial instructions can be in color, greyscale or black and white on the display 120. The instructions can be text. For example, the instructions displayed for a stage of treatment can read "expose bare chest," "attach pads," "start CPR," "shock delivered," and so on depending on the stage of treatment during the resuscitation process. In some examples, the display 120 can display both the pictorial instructions and the textual instructions simultaneously for a stage of treatment. In some examples, an audio instruction can accompany the pictorial and textual instructions. As discussed herein, the user can toggle between the operating modes, and thus the different mode-specific series of instructions being displayed, at any stage of treatment.

One or more statistics or information of the treatment can be shown during any stage. For example, in FIGS. 3-13, the instructions show several statistics of the current treatment of the patient. One statistic shown in the examples is the lightning symbol of the shock button 170 next to a number representing the number of times the shock therapy has been delivered. For example, when a shock is delivered to the patient, the number next to the lighting symbol can be incremented by one. In some examples, a statistic can be a measurement of time elapsed since the beginning of the treatment, so that a rescuer is better able to time the application of appropriate therapies.

Operating the AED for treatment of the patient can have several stages during a resuscitation process, which are described in further detail below. Once the AED is powered on, the user can check the readiness indicator 160 to determine whether the AED is ready to use. Once the AED is powered on, the AED can detect what kind of electrode assembly is attached via the port 180 and enter the operating mode which is appropriate. In some examples, the AED can instruct the user how to prepare the patient for treatment with the electrode assembly.

Figure 3:
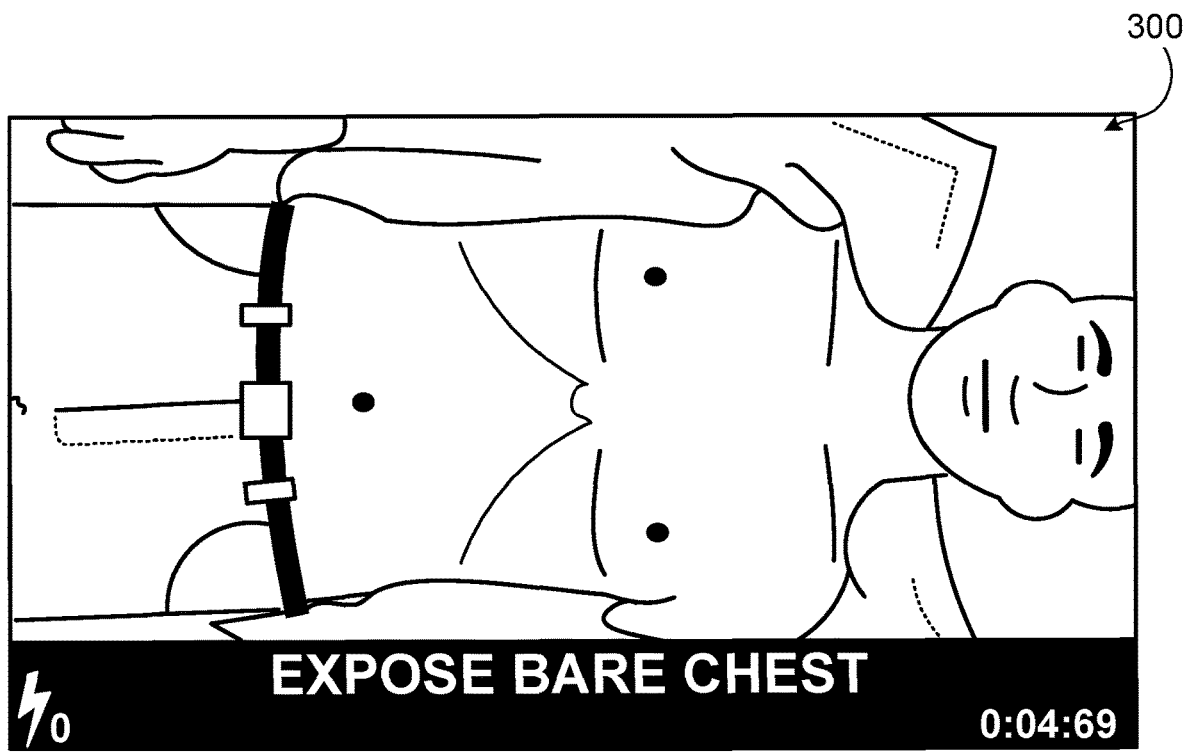
Figure 4:
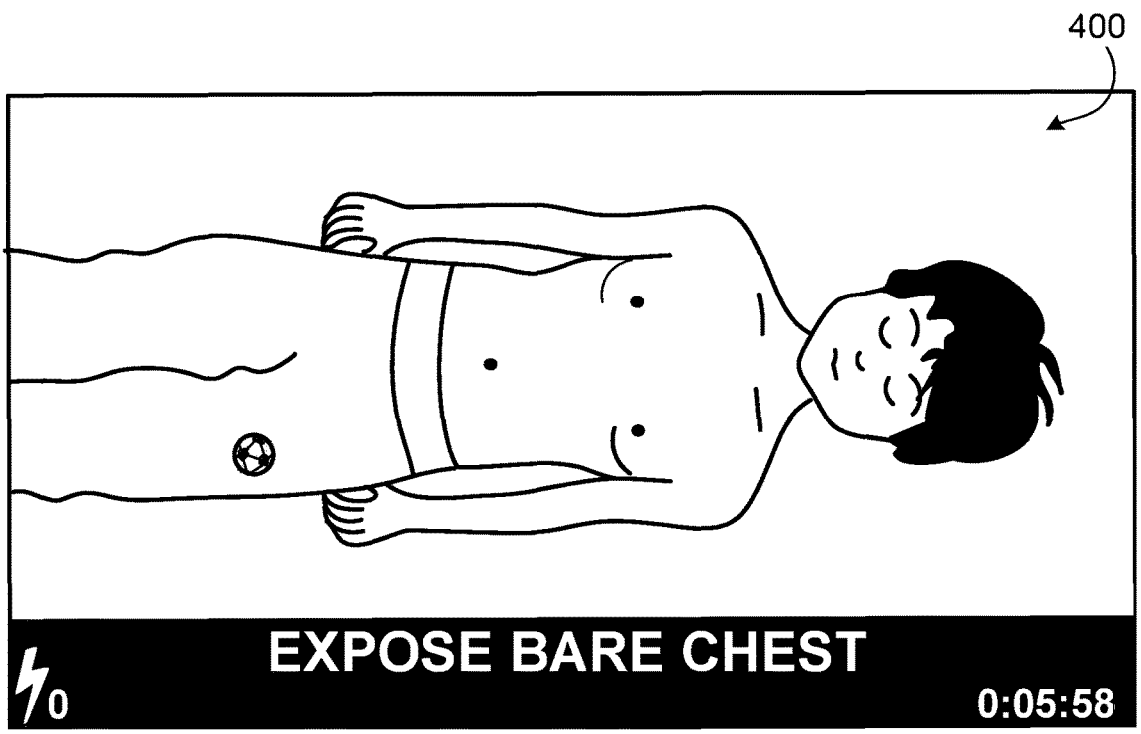

FIGS. 3-4 show examples of an instruction 300, 400 for preparing the patient (e.g. the patient preparation stage). FIG. 3 shows the instruction for exposing the bare chest for the mode-specific series of instructions for the adult patient. Since each piece of the electrode assembly can be placed on the chest of the adult patient during treatment, the instructions can show that a shirt need not be entirely removed from the adult patient. FIG. 4 shows a version of the same stage of instruction for the mode-specific series of instructions for the pediatric patient. For example, the image shows that the shirt of the pediatric patient has been entirely removed from the pediatric patient. During treatment, a piece of the electrode assembly may need to be placed on the back of the pediatric patient, and so the shirt of the pediatric patient may inhibit treatment if it is not removed by the user. The images and text of the stage of instructions can be accompanied by audio prompts. For example, the audio prompt for the adult operating mode instruction of FIG. 3 can include instructions such as "expose bare chest," "cut or tear clothing to expose patient's bare chest," or similar text. In some examples, the audio prompt for the pediatric patient mode instruction of FIG. 4 can include the instructions such as "completely remove the child's shirt, cutting or tearing if needed" or similar instructions.

Figure 5:
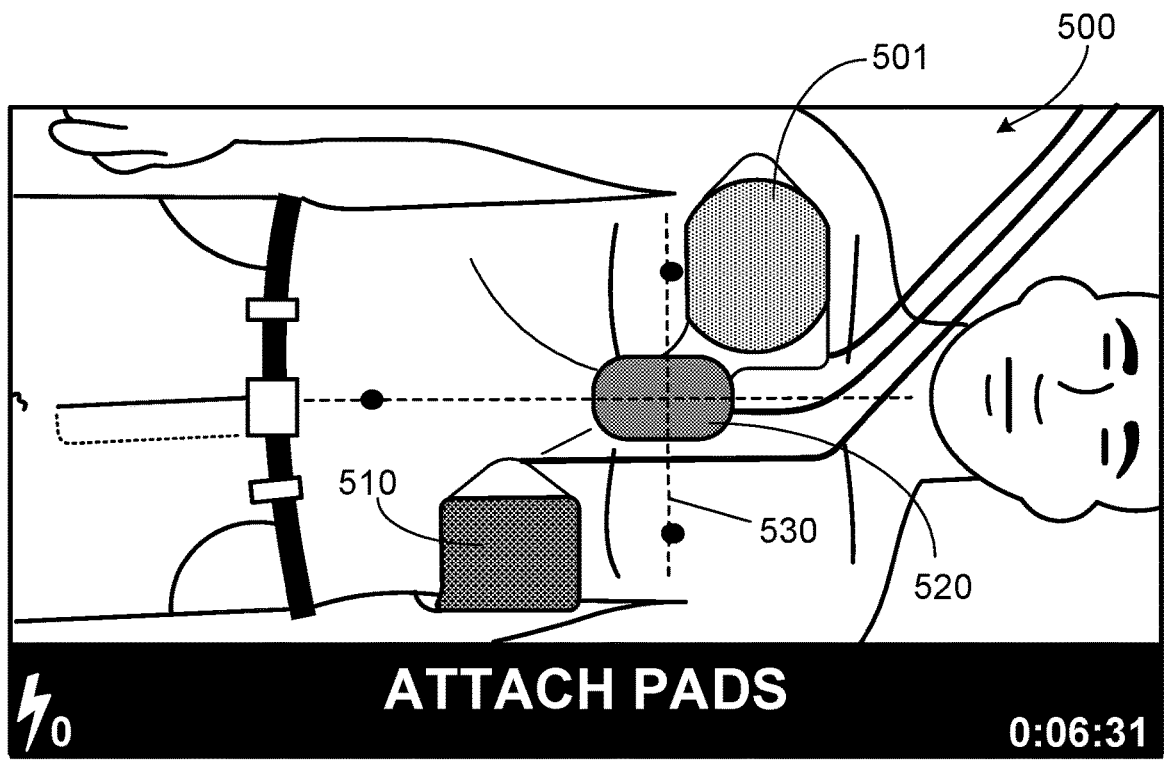
Figure 6:
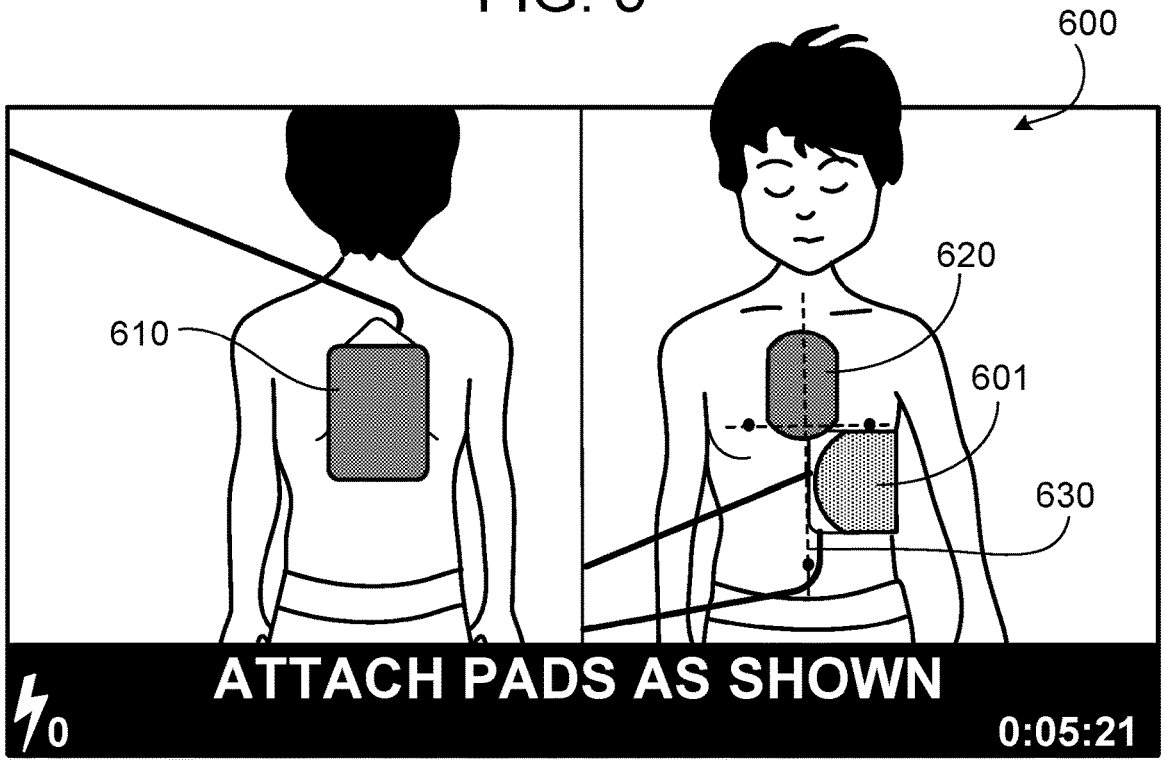

FIGS. 5-6 show examples of instructions 500, 600 for placement of the electrode assembly on the patient for different types of patients (e.g. the electrode placement stage). FIG. 5 shows an example of an electrode placement instruction 500 from the mode-specific series of instructions for the adult patient. The instruction can appear on the display 120. The instruction can appear on the display 120 after the patient has been instructed to remove the electrode assembly from a packaging. The patient's bare chest is exposed for placement of the electrode assembly. The electrode assembly is removed from packaging and the backing of each electrode is removed to expose the adhesive on the bottom surface of each electrode. An electrode 501 is placed on the chest of the patient. The electrode 501 can typically be placed on the right side of the adult patient's chest. The placement of the electrode 501 can be assisted by the placement of an attached chest compression sensor 520. The chest compression sensor 520 can have a pattern, such as a dashed cross, on a top surface which guides the user for placing the chest compression sensor 520 on the adult patient. The chest compression sensor 520 is typically placed in the approximate center of the adult patient's sternum. The user can orient the pattern on the chest compression sensor 520 with an imaginary cross 530 on the adult patient's chest and body. For example, a line can be imagined, drawn from the adult patient's chin to the adult patient's belly button intersecting with a line drawn across the adult patient's chest to form an approximate cross 530 as shown in FIG. 5. The user can place and orient the chest compression sensor 520 such that the center or pattern of the sensor approximately corresponds with the intersecting point of the cross 530. Such placement can correspond with where the user will perform chest compressions on the patient during CPR treatment. The instruction can show text such as "attach pads as shown," "attach pads to patients bare chest," or similar.

In some examples, if the electrode 501 is attached to the chest compression sensor 520, the electrode 501 may be automatically oriented to the approximate correct location for treatment on the chest of the adult patient if the chest compression sensor 520 was placed and oriented as described above. In some examples, after the user has properly oriented and positioned the chest compression sensor 520 and electrode 501 on the adult patient's chest, the user can press the chest compression sensor 520 and electrode 501 into the skin of the adult patient so that the adhesive affixes the electrode 501 and chest compression sensor 520 firmly in place. A second electrode 510 is affixed to the adult patient on an intercostal region. As shown in FIG. 5, the electrode 510 can be affixed to a lower left intercostal region of the adult patient such that the electrode 510 wraps around the left intercostal muscles. Once the electrodes 501 and 510 have been affixed to the adult patient, the patient may be ready for treatment. If the user desires feedback on performing chest compressions during CPR, the chest compression sensor 520 can be affixed to the patient as described above.

FIG. 6 shows an example of an electrode placement instruction 600 from the mode-specific series of instructions for the pediatric patient. The instruction can appear on the display 120. The patient's bare chest is exposed for placement of the electrode assembly 100. The electrode assembly is removed from packaging and the backing of each electrode is removed to expose the adhesive on the bottom surface of each electrode. An electrode 601 is placed on an intercostal region of the pediatric patient. As shown in FIG. 6, the electrode 601 can typically be placed on a lower left side of an intercostal region of the pediatric patient such that the electrode wraps around the patient's left intercostal muscles. The placement of the electrode 601 can be assisted by the placement of an attached chest compression sensor 620. The chest compression sensor 620 can have a pattern, such as a dashed cross, on a top surface which guides the user for placing the chest compression sensor 620 on the pediatric patient. The chest compression sensor 620 is typically placed in the approximate center of the pediatric patient's sternum. The user can orient the pattern on the chest compression sensor 620 with an imaginary cross 630 on the pediatric patient's chest and body. For example, a line can be imagined, drawn from the pediatric patient's chin to the pediatric patient's belly button intersecting with a line drawn across the pediatric patient's chest to form an approximate cross 630 as shown in FIG. 6. The user can place and orient the chest compression sensor 620 such that the center or pattern of the sensor approximately corresponds with the intersecting point of the cross 630. Such placement can correspond with where the user will perform chest compressions on the patient during CPR treatment. The instruction of FIG. 6 can include text saying "attach pads to child's back and chest," "attach pads as shown," or similar.

In cases where the electrode 601 is attached to the chest compression sensor 620, the electrode 601 may be automatically oriented to the approximate correct location for treatment on an intercostal region of the pediatric patient if the chest compression sensor 620 was placed and oriented as described above. In some examples, after the user has properly oriented and positioned the chest compression sensor 620 and electrode 601 on the pediatric patient's body, the user can press the chest compression sensor 620 and electrode 601 into the skin of the pediatric patient so that the adhesive affixes the electrode 601 and chest compression sensor 620 firmly in place. A second electrode 610 is affixed to the pediatric patient on the patient's back. As shown in FIG. 6, the electrode 610 is affixed to the approximate center of the pediatric patient's back. Once the electrodes 601 and 610 have been affixed to the pediatric patient, the patient may be ready for treatment. If the user desires feedback on performing chest compressions during CPR, the chest compression sensor 620 can be affixed to the patient as described above.

The first electrode 501, 601, the second electrode 510, 610, and the chest compression sensor 530, 630 can each be represented as a shaded object in the instructions. The color of the shading for the object can match a background color of piece of the electrode assembly represented by the object, such as the first electrode 501, 601, the second electrode 510, 610, or the chest compression sensor 530, 630. The relative shapes and sizes of the objects in the instructions can match the shapes, sizes, or both for each piece of the electrode assembly. The instructions on the display 120 can match or be consistent with instructions on the electrode assembly, electrode assembly packaging, or both. Such consistency can help the user associate the electrode assembly with the AED and facilitate use of the electrode assembly with the AED. The instruction can show text such as "place pads as shown" or similar.

Figure 7:
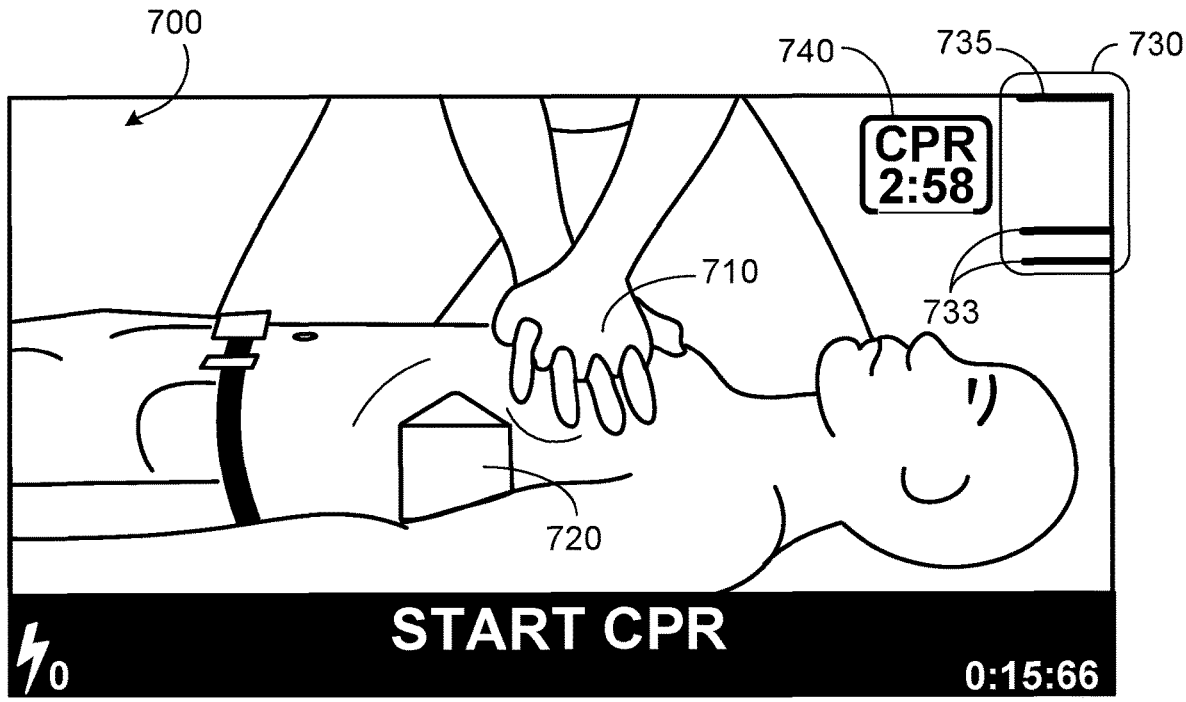
Figure 8:
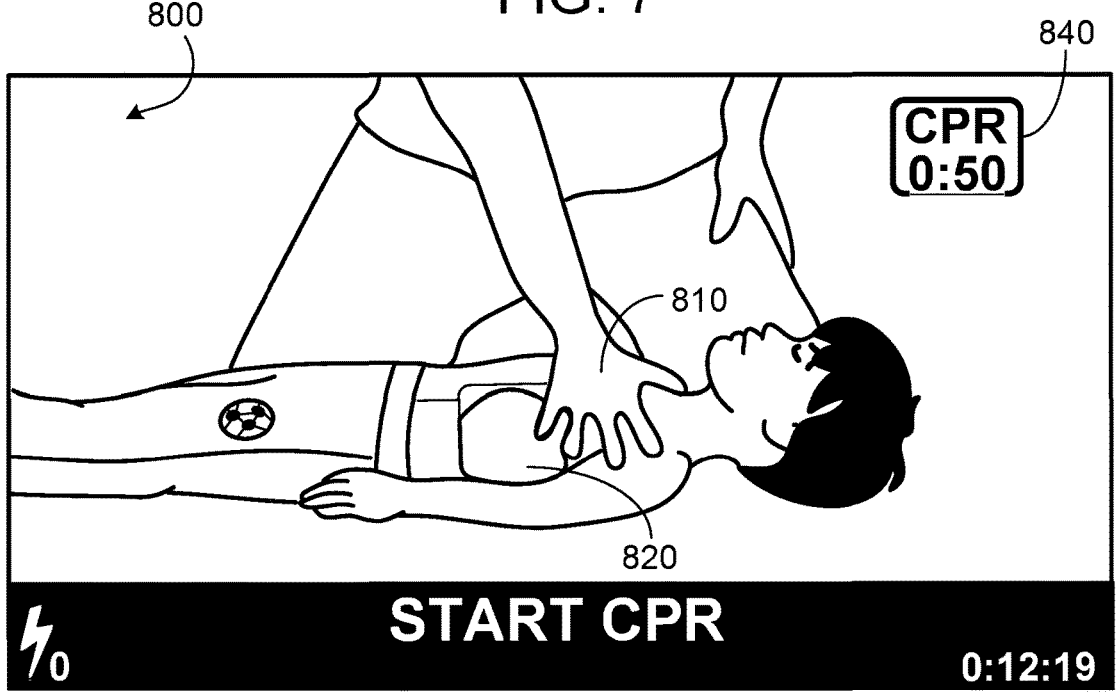

FIGS. 7-8 show examples of user instructions 700, 800 for performing CPR for different mode-specific series of instructions, such as the adult and pediatric instructions (e.g the CPR therapy stage). FIG. 7 shows an example adult CPR instruction 700 for performing CPR from the mode-specific series of instructions for adult patients. The instruction 700 can include one or more of pictorial instructions, textual instructions, and auditory instructions. The instruction 700 can appear on the display 120.

The adult user configuration CPR instruction 700 can include CPR instructions as one or more pictorial instructions. For example, the CPR instruction 700, as shown in FIG. 7, shows the approximate hand placement for compressing the adult patient's chest during CPR. For example, the instruction 700 shows both the user's hands 710 on the center of the adult patient's chest with fingers interlocked. The user is hunched over the patient such that the user can apply compression force with the user's full weight. The electrode 720 is visible on the left side of the intercostals of the adult patient. The color, size, and shape are approximately consistent with the adult instructions for electrode placement (e.g. as shown in FIG. 5, above). The electrode can be depicted as faded, discolored or otherwise inconspicuous so as to deemphasize the importance of the electrode during CPR.

The adult CPR instruction 700 shows a compression feedback meter 730. The meter 730 can provide CPR feedback, such as in the form of an animated measurement, of the user's compression of the chest of the adult patient when the chest compression sensor 530 is present. In one example, the meter 730 can be two static bars 733 and a third bar 735. In some examples, the two static bars 733 can represent an approximate suggested range of compression of the chest of the adult patient. The suggested range of chest compression for the adult patient may be set according to the most recent American Heart Association Guidelines for CPR (e.g., between 2.0 and 2.4 inches). The third bar 735 can represent a measured approximate depth of the compression of the chest of the patient. Hence, the rescuer may be advised to apply chest compressions such that the third bar 735 remains within the region located between the two static bars 733. In some examples, the area above the third bar 735 can be shaded to illustrate a bar graph, rather than a single line, for assisting the user in visualizing the approximate measured depth of the compression being performed. The three bars can be approximately parallel. In an example representation of chest compression, the third bar 735 can move within and outside of the range of the two static bars 733. For example, when the chest of the adult patient is not compressed, the third bar 735 can be at approximately the same position on the display 120 as the top of the display. When the chest is compressed, then the third bar 735 may move down according to the depth of the compressions. In some cases, the third bar 735 (or other bars or portions of the display) may be color coded depending on whether the compressions are within the desired range (e.g., according to AHA guidelines). For instance, when the compressions are within the desired range, one or more of the bars or other portions of the screen may be colored green (or another affirmative indicating color), though, when compressions are outside of the desired range, one or more of the bars or other portions of the screen may be colored red (or another color indicating an undesirable result). In one example, when the user compresses the chest of the adult patient, the third bar 735 can move down the display 120 toward the two static bars, which can provide a visual representation of the depth of the compression performed by the user. For example, the deeper the chest compression of the adult patient is measured, the lower the third bar 735 can move on the display 120. The meter 730 can change colors when the measured chest compression is outside the suggested range of chest compression for an adult. For example, the meter 730 can be a bright pink or green or other color indicating an affirmation in CPR performance when the chest compressions are within the approximate suggested chest compression range. When the measured chest compressions are out of the suggested range, the meter 730 can turn a dark purple, yellow, red or other color indicating that the CPR applied needs to change. The chest compression feedback can include one or more of visual, auditory, textual, and haptic feedback. In general, CPR feedback may be provided in accordance with the latest American Heart Association (AHA) Guidelines for Cardiopulmonary Resuscitation and Emergency Cardiovascular Care.

The adult CPR instruction 700 can show a timer 740. In one example, the timer 740 can display the time elapsed since initiation of the CPR stage of treatment. Alternatively, the timer 740 may display the amount of time remaining in the CPR interval. In some examples, the timer 740 can countdown the appropriate time for the CPR stage of treatment before the user should progress to another stage of treatment such as ventilation, electric shock therapy or ECG measurement. The display may further show the elapsed event time (shown in the lower right corner of the figure), indicating the amount of time that has elapsed since the start of rescue and/or when the defibrillator is powered on.

Upon the cessation of chest compressions, the CPR instruction display may also show an idle timer, to provide the user with an indication of the time elapsed since CPR chest compressions have stopped. When the idle timer shows that a significant amount of time has elapsed, the rescuer may be more motivated to apply chest compressions to the patient. In some embodiments, the device may provide a series of escalating alerts to the rescuer to continue chest compressions based on how much time has elapsed as indicated by the idle timer.

The adult CPR instruction 700 can include textual instructions. Textual instructions on the display 120 can change depending on the measured compression depth. For example, the textual instruction can read "push harder" if the compressions are too shallow, "reduce pressure" if the compressions are too deep, "good compression," "increase pace" if the compressions are being performed too infrequently, "push to match tone," "open airway," "check breathing," "continue CPR," stop CPR," "breathe during CPR," and so forth.

The adult CPR instruction 700 can include one or more auditory instructions. The speaker 140 can provide such instructions. The speaker 140 can emit a metronome sound at regular intervals, such as a click, beep, tone, or other sound. The metronome sound can be at a pace that represents an approximate suggested pace (e.g., approximately 100 compressions per minute) for providing chest compressions during CPR. The speaker 140 can emit spoken instructions which are relevant to the CPR treatment. For example, the spoken instructions can include "push harder" if the compressions are too shallow, "reduce pressure" if the compressions are too deep, "good compression," "increase pace" if the compressions are being performed too infrequently, "push to match tone," "open airway," "check breathing," "continue CPR," stop CPR," "breathe during CPR," and so forth.

FIG. 8 shows an example pediatric CPR instruction 800 that may be included in a user configuration corresponding to a pediatric operating mode. The instruction 800 can include one or more of pictorial instructions, textual instructions, and auditory instructions. The instruction 800 can appear on the display 120.

The pediatric CPR instruction can include one or more pictorial instructions. For example, the CPR instruction 800, as shown in FIG. 8, shows the approximate hand placement for compressing the pediatric patient's chest during CPR. For example, the instruction 800 shows one of the user's hands 810 on the chest of the pediatric patient with fingers spread and the palm in contact with the chest. The user's other hand can help support the user's weight such that not all of the weight of the user is used to help compress the chest of the pediatric patient. The electrode 820 is visible on the left side of the pediatric patient's intercostal. The electrode is faded, discolored or otherwise inconspicuous so as to deemphasize the importance of the electrode during CPR.

The pediatric CPR instruction 800 can show a timer 840. In one example, the timer 840 can display the time elapsed since initiation of the CPR stage of treatment. In some examples, the timer 840 can countdown the appropriate time for the CPR stage of treatment before the user should progress to another stage of treatment such as ventilation, electric shock therapy or ECG measurement. Similar to that discussed above with respect to adult CPR instructions, the CPR instruction may also show an idle timer that appears upon the cessation of chest compressions, which provides an indication of the time elapsed since CPR chest compressions have stopped.

The pediatric CPR instruction 800 can include textual instructions. Textual instructions on the display 120 can change depending on the measured compression depth. For example, the textual instruction can read "push harder" if the compressions are too shallow, "reduce pressure" if the compressions are too deep, "good compression," "increase pace" if the compressions are being performed too infrequently, "push to match tone" "open airway," "check breathing," "continue CPR," stop CPR," "breathe during CPR," and so forth. The pediatric CPR instruction 800 can include one or more auditory instructions. For example, the speaker 140 can provide these instructions. The speaker 140 can emit spoken instructions which are relevant to the CPR treatment. For example, the spoken instructions can include "push harder" if the compressions are too shallow, "reduce pressure" if the compressions are too deep, "good compression," "increase pace" if the compressions are being performed too infrequently, "push to match tone," "open airway," "check breathing," "continue CPR," stop CPR," "breathe during CPR," and so forth. Though, in some implementations, chest compression feedback, such as the above described textual instruction, meter 730, or other chest compression feedback may be omitted from the pediatric CPR instruction 800. Pediatric patients can vary in size (e.g., depending on age) and the recommended chest compression depths can vary such that a suitable recommendation for chest compression may be difficult to precisely determine. In some examples, in the user configuration corresponding to the pediatric operating mode, the AED can refrain from providing part or all of the chest compression feedback. For example, the AED may provide only feedback on the timing of chest compressions and refrain from providing feedback on compression depth. Yet, when the AED is operating in the adult operating mode, the user configuration may include chest compression feedback as discussed above.

The speaker 140 can emit a metronome sound at regular intervals, such as a click, beep, tone, or other sound. The metronome sound can represent an approximate suggested pace (e.g., approximately 100 compressions per minute) for providing chest compressions during CPR.

Figure 9A:
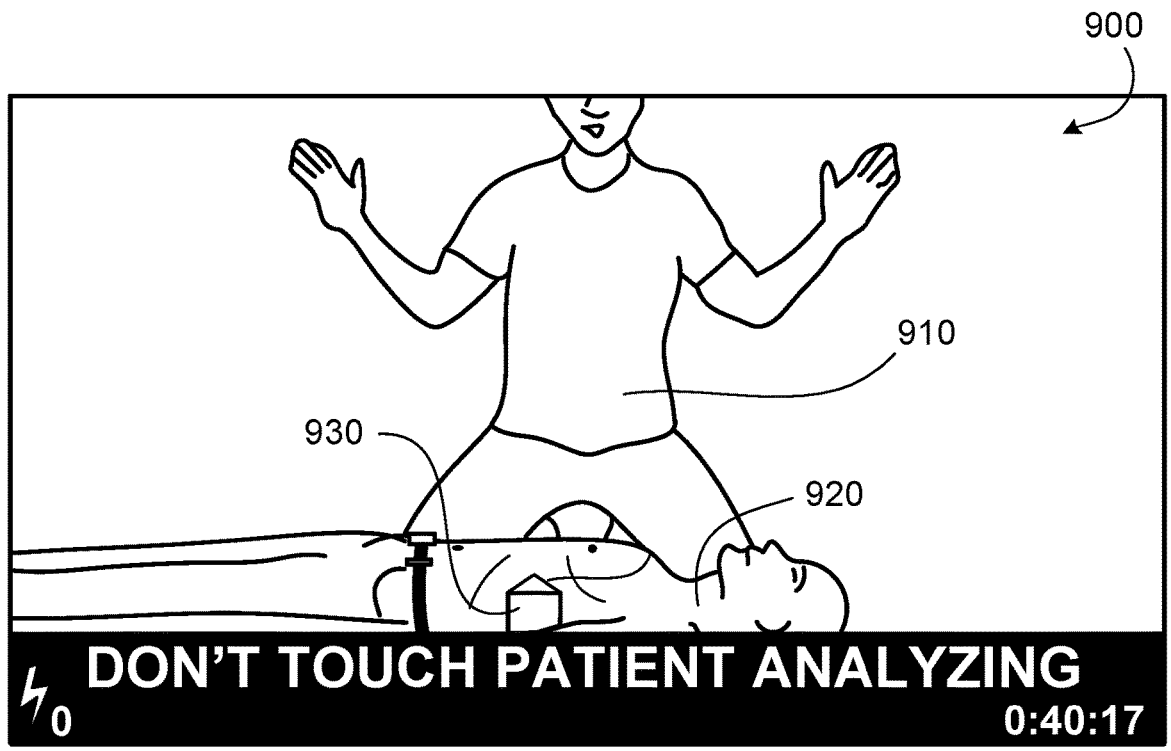
Figure 9B:
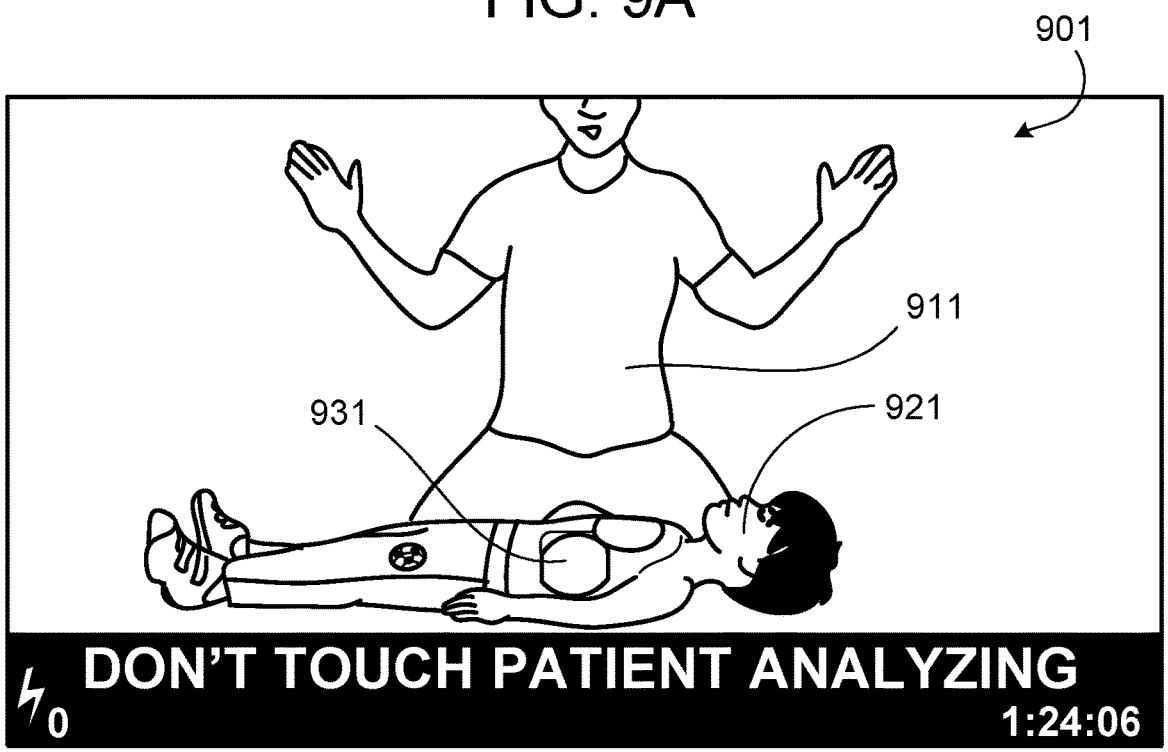
Figure 9C:
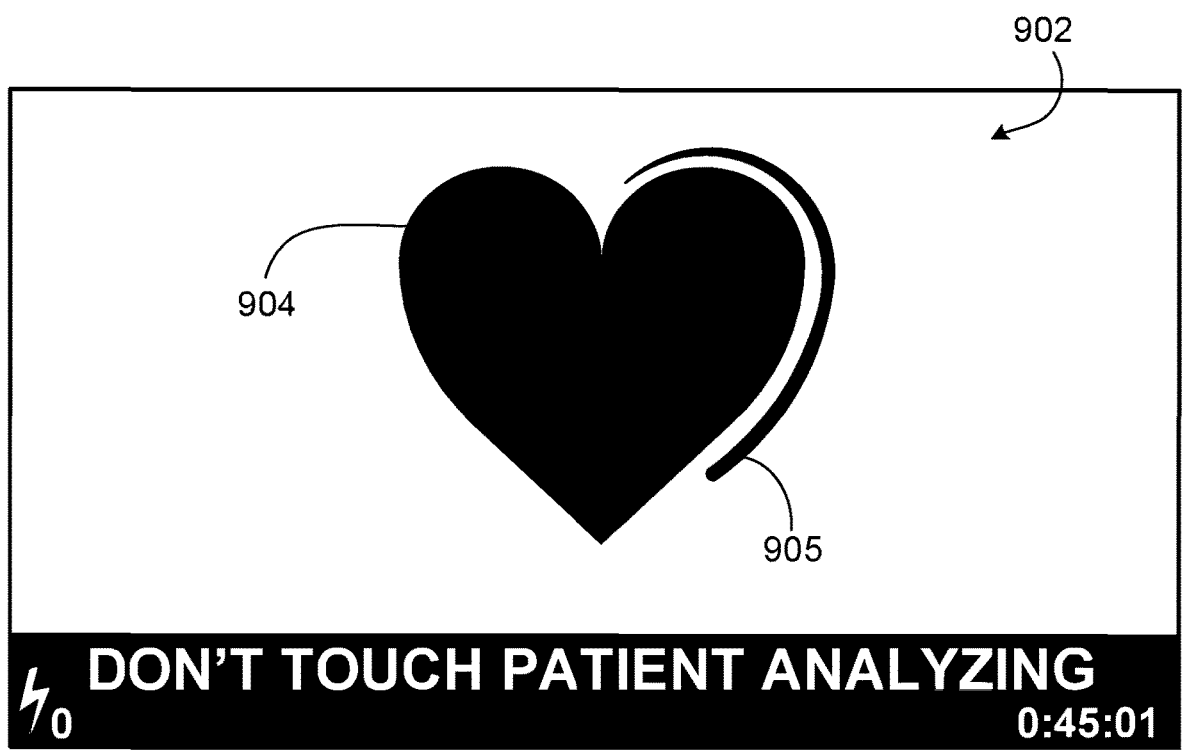

FIGS. 9A-9C show examples a shock therapy cycle. FIG. 9A shows an example of an analyzing instruction 900 for the mode-specific series of instructions for the adult patient. The instruction 900 can include one or more of pictorial instructions, textual instructions, and auditory instructions. The instruction 900 can appear on the display 120. For example, the analyzing instruction 900 can display while the AED 100 measures the adult patient's ECG signal to determine whether to prepare the AED to deliver an electric shock to the patient through the electrode assembly. The user 910 is shown to be away from the adult patient 920 such that the user is not in contact with the adult patient. The user 910 can be advised not to contact the patient 920 while the patient's ECG signal is being analyzed to determine whether a shockable or non-shockable ECG rhythm exists. In some examples, it is possible for such contact to disrupt the measurement of the patient's ECG signal. The user 910 can be shown with his hands up and away from the patient 920. The electrode 930 is visible on the adult patient's abdomen. The color, size, and shape are approximately consistent with the adult instructions for electrode placement (e.g. as shown in FIG. 5, above). The electrode can be represented inconspicuously so as to deemphasize the importance of the electrode during the analyzing stage of treatment.

The analyzing instruction 900 can include textual instructions. Textual instructions which are relevant to the analyzing stage can appear on the display 120 and can change depending on the measured vitals. For example, the textual instruction can read "don't touch patient analyzing" during analysis, "re-attach electrodes" if the electrodes detach from the patient, "plug in pads cable" if the cable detaches from the port 180, "shock advised," "no shock advised," "check responsiveness," "call for help," and so forth.

The analyzing instruction 900 can include one or more auditory instructions. The speaker 140 can provide such instructions. The speaker 140 can emit spoken instructions which are relevant to the analyzing stage of treatment. For example, the textual instruction can read "don't touch patient analyzing" during analysis, "re-attach electrodes" if the electrodes detach from the patient, "plug in pads cable" if the cable detaches from the port 180, "shock advised," "no shock advised," "check responsiveness," "call for help," and so forth.

FIG. 9B shows an example of an analyzing instruction 901 for the mode-specific series of instructions for the pediatric patient. The instruction 901 can be similar to the instruction 900, though a pediatric patient 921 is depicted rather than an adult patient (e.g., the adult patient 920 shown in FIG. 9A). The instruction 901 can include one or more of pictorial instructions, textual instructions, and auditory instructions which are similar to the adult analysis instructions 900. The electrode 931 is visible on the left side of the pediatric patient's The color, size, and shape are approximately consistent with the pediatric instructions for electrode placement (e.g. as shown in FIG. 6, above). intercostal. The color, size, and shape are approximately consistent with the pediatric instructions for electrode placement (e.g. as shown in FIG. 6, above). The electrode is inconspicuously shown and can be represented as faded as to deemphasize the importance of the electrode during the analyzing stage of treatment.

FIG. 9C shows an example of an alternative analyzing instruction 902 for the analysis stage. The instruction 902 can be displayed in any operating mode, such as the pediatric operating mode and the adult operating mode. In the example of FIG. 9C, a symbol, such as a heart 904, is displayed which has a cursor 905 nearby. In some examples, the cursor 905 can be animated. For example, the cursor can move around the heart 904 to indicate to the user that the AED is analyzing the patient's ECG, processing the results, or otherwise performing analysis. The instruction 902 can include one or more of pictorial instructions, textual instructions, and auditory instructions which are similar to the adult analysis instructions 900 and the pediatric analysis instructions 901.

In some implementations, a voting scheme can be employed to determine the presence or absence of shockability. A voting scheme uses fixed-length time segments. For example, data corresponding to three separate segments of ECG data can be processed to label the segments as either shockable or non-shockable, and the final decision can be based on the labels corresponding to at least two of the three labels. If the first two segments are labelled as shockable, the voting scheme can be terminated and the presence of a shockable rhythm can be identified. If the first segment is labelled as shockable and the second is labeled as non-shockable, a third segment is evaluated. In such a voting scheme, each segment is typically of fixed length, e.g., three seconds. Thus, when only using such a voting scheme, a minimum amount of time elapses before a determination can be made of whether a patient is in a shockable or non-shockable state. For example, if three-second segments are used, at least six seconds, and up to nine seconds, elapses before a determination can be made.

In contrast, in some implementations, the delay inherent in a voting scheme can be avoided, for example, by using high-accuracy clauses in determining the presence or absence of shockable rhythm. A clause is an expression that defines constraints on features of an ECG waveform underlying the ECG data; a clause is said to be met (or satisfied) if the criteria of the clause are met by the features of the ECG waveform being analyzed. In particular, if the criteria are met, then the ECG rhythm is said to be shockable or non-shockable, depending on the particular clause. High accuracy (e.g., low false positive rate) clauses may be created or defined in various ways. Using such high accuracy clauses can allow for identifying the presence or absence of shockable rhythms within a short time window (e.g., less than one second) thereby reducing analysis time as compared to, for example, the analysis time associated with a voting scheme. In some implementations, the high-accuracy clauses are determined heuristically by testing various candidate clauses for accuracy against a database of pre-stored patient data to determine clauses that have low false positive rates. In some implementations, the clauses can be determined, for example, by using a machine learning process on the database to identify conditions that indicate the presence of shockable rhythms with low false positive rates.

A clause that applies to an adult patient may be inapplicable to a pediatric patient and vice-versa. For example, because a pediatric patient typically has a higher heart rate than an adult patient, the characteristics of a pediatric patient's ECG waveform will be different than an adult patient's. Thus, a different set of clauses may be used when a defibrillator is in a pediatric operating mode versus an adult operating mode. In this way, the analysis of the ECG signal differs when in the pediatric operating mode versus an adult operating mode. Further, while the voting scheme described above can be applied to both pediatric patients and adult patients, in some implementations, the technique of using high accuracy clauses is typically only applied to adult patients (e.g., used in an adult operating mode).

Although the use of high-accuracy clauses tends to be faster than the use of a voting scheme, a voting scheme can still be used in certain situations, e.g., situations in which none of the high accuracy clauses are met and thus cannot be used in making the determination of whether a patient is in a shockable or non-shockable state. For example, normal-accuracy clauses may be used with the voting model described above.

The clauses with a sufficient level of accuracy for a particular time segment length ("high accuracy" clauses), as well as clauses with an insufficient level of accuracy for a particular time segment length ("normal accuracy") are defined with parameters that are calculated by processing ECG data stored in a memory buffer.

In some examples, high accuracy clauses are defined as having a accuracy threshold of 99% for a particular time length (width) of a waveform. In other words, if a clause is associated with a time length of 3 seconds and has an accuracy of at least 99%, the clause is a high accuracy clause.

In some examples, a particular clause is a high accuracy clause if the clause is applied to a portion of an ECG signal meeting a threshold time length (e.g., a length associated with the particular clause) needed to achieve a certain level of accuracy. Further, the same clause may be a normal accuracy clause if the clause is applied to a portion of an ECG signal that does not meet the threshold time length, e.g., the portion of the ECG signal has a length less than the threshold. In this way, as the length of the ECG signal portion increases, accuracy tends to increase as well. Thus, there will be a minimum time segment length below which a clause is only a normal accuracy clause, and is not suitable as a high accuracy clause, but for time segment lengths longer than this minimum time length, the clause is a high accuracy clause.

For instance, there may be clauses for which the minimum time segment length is 1 second, which are termed "1-second clauses." For instance, there may be clauses for which the minimum time segment length is 2 seconds, which are termed "2-second clauses." For instance, there may be clauses for which the minimum time segment length is 3 seconds, which are termed "3-second clauses." Segments for which the minimum time length is 6 seconds are termed "6-second clauses". Some examples of these are listed in Table 1.

TABLE 1

| Clause Timing | Intended Waveforms | Clause Logic | Result |
|---|---|---|---|
| 1 second | Normal sinus rhythm (one clear peak) | Maximum_slope > 200 uv/sample and relative_flatness > 100 | No Shock |
| 1 second | Asystole (low max and min amplitudes) | Max_amplitude < 50 uv and Min_amplitude < −50 uv | No Shock |
| 1 second | Slow VT | Peaks < 3 and average_peak_width > 160 ms | No Shock |
| 1 second | PEA | Maximum_slope < 30 uv/sample and peaks < 3 | No Shock |
| 1 second | VFIB | Peaks > 3 and relative_flatness < 50 | Shock |
| 1 second | Fast VT | Peaks >= 4 and average_peak_width > 160 ms and peak_width_variability < 100 | Shock |
| 2 seconds | AFIB (many peaks but one or more tall peaks) | Maximum_slope > 200 uv/sample and relative_flatness > 80 and peak_tops_amplitude_variability < 250 | No Shock |

TABLE 1-continued

| Clause Timing | Intended Waveforms | Clause Logic | Result |
|---|---|---|---|
| 2 seconds | Slow PEA | Maximum_slope < 50 uv/sample and peak_tops_amplitude_variability < 250 and peak_tops_interval_variablity < 100 | No Shock |
| 2 seconds | VF (many peaks) | Maximum_slope > 50 uv/sample and relative_flatness < 50 and slope_zero_crossings > 20 | Shock |
| seconds | VT (high rate and VT | R-R_interval < 350 ms and QRS_Width > 140 ms and QRS_Width_Variation == 1 | Shock |
| 6 seconds | VT waveform (HR > 150 bpm and wide complexes) | R-R_interval < 400 ms and QRS_Width > 140 ms and QRS_Width_Variation == 1 and flatness < 50 | Shock |
| 6 seconds | irregular PEA rhythm (intermittent flat areas and wide peaks) | flatness > 200 and pos_peak_width > 300 | No Shock |

Some additional 3-second clauses are found in Table 2.

TABLE 2

| Intended Waveforms | Clause Logic | Result |
|---|---|---|
| Few sharp peaks | ((Amplitude Variability < Threshold ) AND (Amplitude > 250 microvolts) AND (Maximum Slope > Threshold)) | No Shock |
| Stable HR and QRS width | ((QRS Rate > 220) AND (Width Variation == Stable) AND (Width < 100 milliseconds)) OR ((SVT) AND (QRS Rate > 245)) | No Shock |
| Stable QRS width | ((Width Variation == Stable) AND (QRS Width < 65) AND (Amplitude > 250) AND (QRS Rate > 300) | No Shock |
| Stable QRS amplitude, large QRS amplitude, clear peaks. HR > 180 | ((Amplitude Variability < Threshold) AND (Amplitude > 500) AND (Amplitude Variability <= Threshold) AND (QRS Variability < Threshold) AND (QRS Rate > 300) | No Shock |

Some additional 6-second clauses can be found in Table 3.

TABLE 3

| Intended Waveforms | Clause Logic | Result |
|---|---|---|
| Asystole waveform with very small electrical activity | (Average amplitude less than 100 microvolts) | No Shock |
| Fast PEA type waveform where HR > 160 with some variability and stable QRS width but maximum slope is low | (QRS Rate greater than 270 BPM) AND (QRS Variability < QRSV_Threshold) AND (Amplitude Variability < AV_Threshold) AND (Maximum Slope < Min_Slope_Threshold) AND (Width Variability > WV_Threshold) | No Shock |

TABLE 3-continued

| Intended Waveforms | Clause Logic | Result |
|---|---|---|
| SVT type waveform, Number of SVT beats exceeds threshold, heart rate < 185, QRS width < 140 ms | ((SVT Beats Detected) OR ((NUMBER_OF_SVT_BEATS > SVT_CNT_Threshold) AND (QRS_Rate > QRS_Rate_Threshold) AND (QRS_Width < QRSW_Threshold)) OR ((NUMBER_OF_SVT_BEATS > SVT_CNT_Threshold) AND (QRS Rate > QRS Rate Threshold 2) AND (QRS_Width < QRS Width Threshold)) | No Shock |

In a typical scenario, a caregiver applies electrodes of a defibrillator to a patient. The defibrillator then collects ECG data, sometimes concurrent with a CPR treatment applied to the patient by the caregiver, or at times upon completion of a CPR treatment cycle or in between CPR treatment cycles. The defibrillator collects and processes ECG data by evaluating clauses against time segments of the collected data. If at least one high-accuracy clause is met, the defibrillator uses the state indicated by the clause (e.g., shockable or non-shockable) to direct the caregiver, or the defibrillating device itself, to administer a shock. In some implementations, in an adult operating mode, a shockable state may be identified in less than 6 seconds and sometimes within 2-3 seconds, within 1 second or less of the patient entering the state based on results of applying the clauses to the time segments of data. Other times, a three-step voting scheme employing fixed-length time segments predetermined prior to analysis is used, which may take at least 6-9 seconds or more to identify the patient's current state. In some implementations, a pediatric operating mode only uses the three-step voting scheme.

In some examples, the caregiver may halt the CPR treatment (e.g., due to express instruction to halt CPR treatment, during the natural course of repetitive CPR treatment, and/or during ventilations) while some of the data after completion of CPR treatment is being collected and analyzed for further confirmation of an initial determination of whether the rhythm is shockable or not shockable. Confirmation of an initial determination of shockability is sometimes referred to as a reconfirmation mode which may allow for filtered, eliminated or otherwise reduced CPR artifact in the signal during analysis, but it may pose a potential danger to the patient depending on how long the CPR treatment is halted. Thus, if the evaluation of clauses against time segments of the data is successful in determining the state of the patient after a relatively short amount of time, e.g., less than 6 seconds, the CPR treatment can resume relatively quickly, reducing risk to the patient. In some examples, reconfirmation mode is only available for adult patients, e.g., only available in an adult operating mode.

FIGS. 10A-10D and FIG. 11 show examples of instructions during the shock therapy stage of treatment. During the shock therapy stage, the capacitors can charge to a specified energy level (e.g. a voltage). When an electric shock is desired, the capacitors can discharge through the electrode assembly such that current can pass between the electrodes of the electrode assembly. The specified energy level can be different for different patients. In some examples, the pediatric patient can require a lower energy level than the adult patient.

Figure 10A:
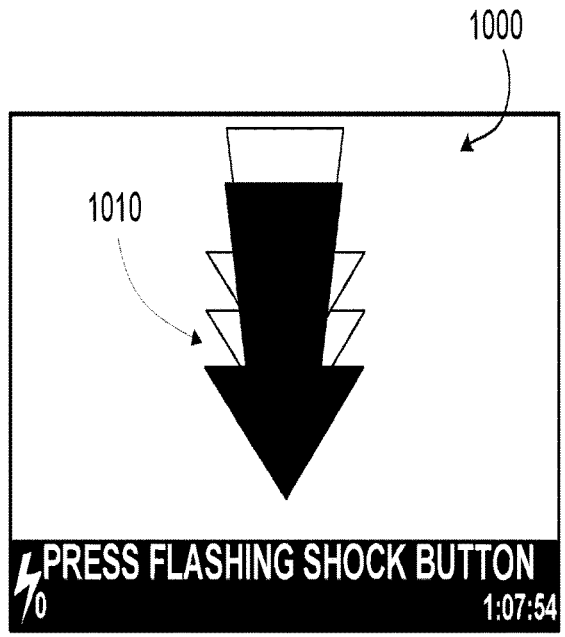

FIG. 10A shows an example of an instruction 1000 displayed if an electric shock is recommended. The instruction can be shown on the display 120 and can include pictorial, textual, and auditory instructions. In some examples, the instruction can include a bright, vibrant color (e.g. orange, red, or similar). In some examples, the bright vibrant color can match the color of the shock button 170 such that the user can associate the shock button 170 with the instruction 1000. The bright vibrant color can serve as a warning to the user to proceed with caution. The instruction 1000 can include a large arrow 1010. The large arrow 1010 can be animated. For example, the arrow can move in a downward motion to suggest a pressing motion. In some examples, the instruction 1000 is skipped and the AED can automatically begin a countdown to electric shock.

The instruction 1000 can include textual instructions. For example, the textual instruction can advise a user to "press flashing shock button," "press shock button," "press shock button semi," "press shock button fully," or the like. The textual instruction can be delivered in auditory form, as discussed above.

Figure 10B:
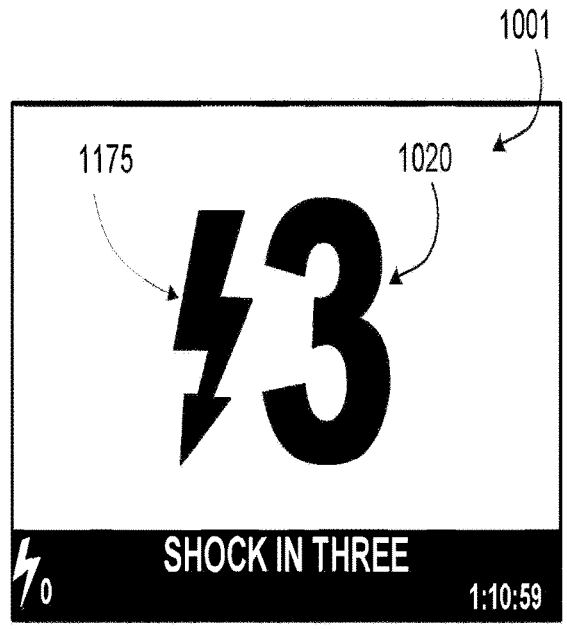
Figure 10C:
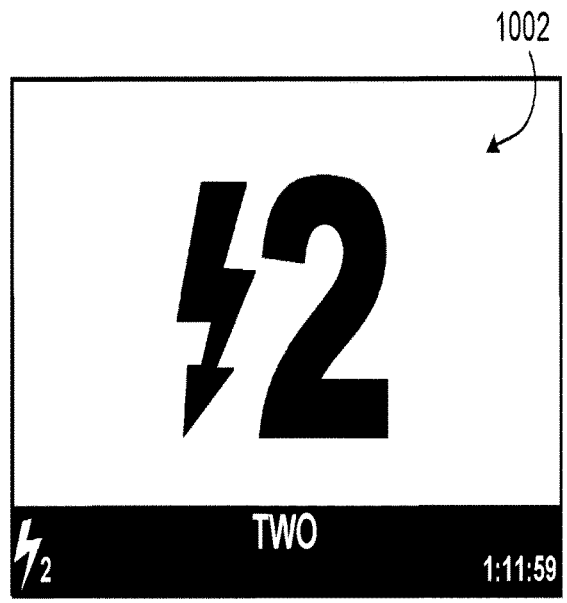
Figure 10D:
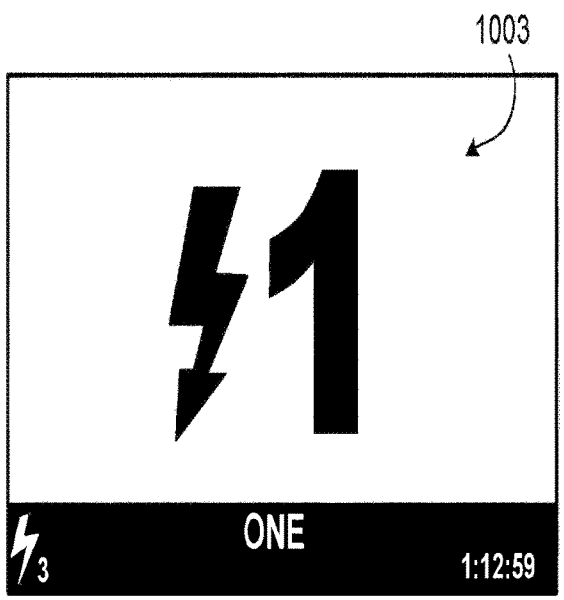

FIGS. 10B-10D show examples of a countdown during the electric shock therapy stage. In some examples, once the shock button has been pressed, the instructions in FIGS. 10B-10D can be shown in sequence to count down to the moment when the electric shock can occur. In some examples, the countdown can begin immediately once the computer processor determines that the electric shock is recommended. The countdown can serve as a safety measure such that the user is not accidentally shocked by the AED when handling the electrode assembly. The instructions can include large numerical digits 1020 which decrease in value in subsequent instructions. For example, the AED can countdown from three to two to one before shocking. The numerical digits 1020 can be accompanied by the shock symbol 1175. The shock symbol 1175 can match a symbol on the shock button 170. The shock symbol can be a symbol which connotes a relationship to electricity, such as a lightning bolt. In some examples, the countdown can be halted for various reasons, such as the pads disconnecting, AED malfunction, an abort by the user, and so on. If the computer processor detects that the electrode assembly has detached from the patient or is improperly configured, the AED may return to the electrode assembly configuration stage.

Figure 11:
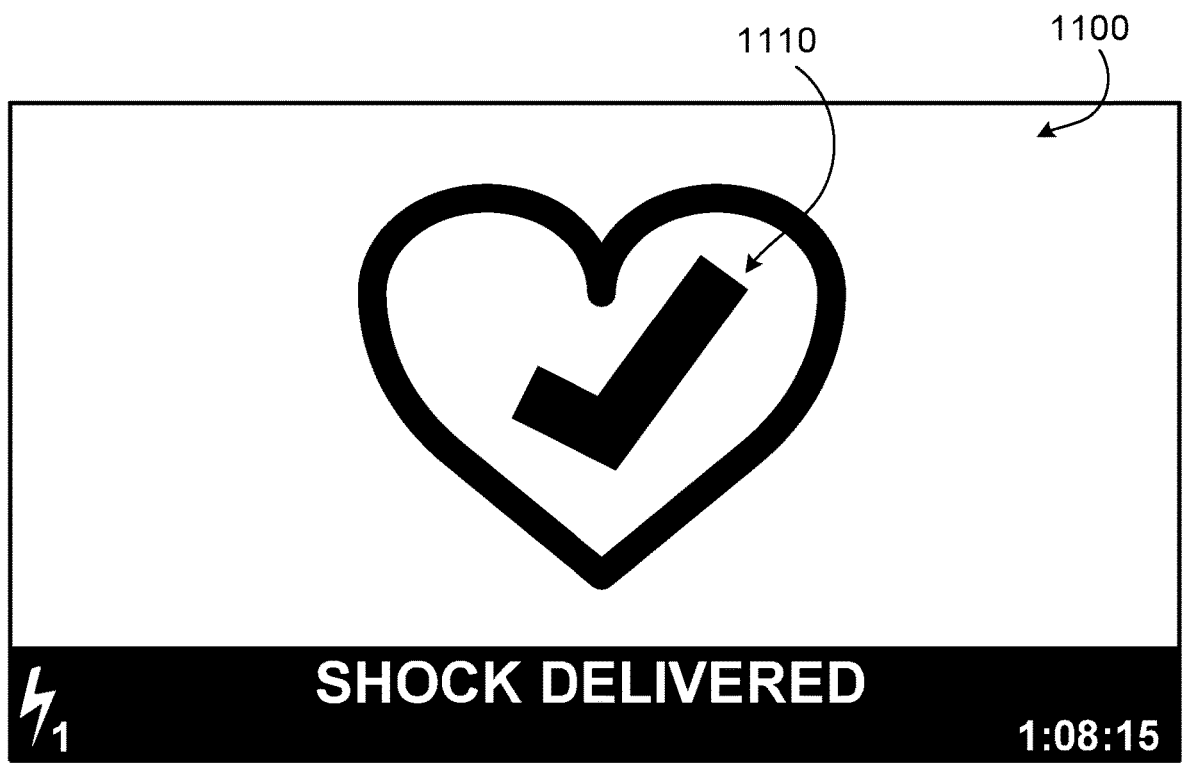

In some examples, once the countdown is completed the AED can administer the electric shock. In some examples, the electric shock can be applied immediately when the shock button 170 is pressed. Once the electric shock has occurred, a confirmation screen 1100 can be displayed. An example of the confirmation screen is shown in FIG. 11. A checkmark 1110 or other confirmatory symbol can be displayed. The confirmation can include a textual confirmation, such as "shock delivered, shock complete," and so forth. The AED can then repeat one or more stages of treatment as needed.

Figure 12:
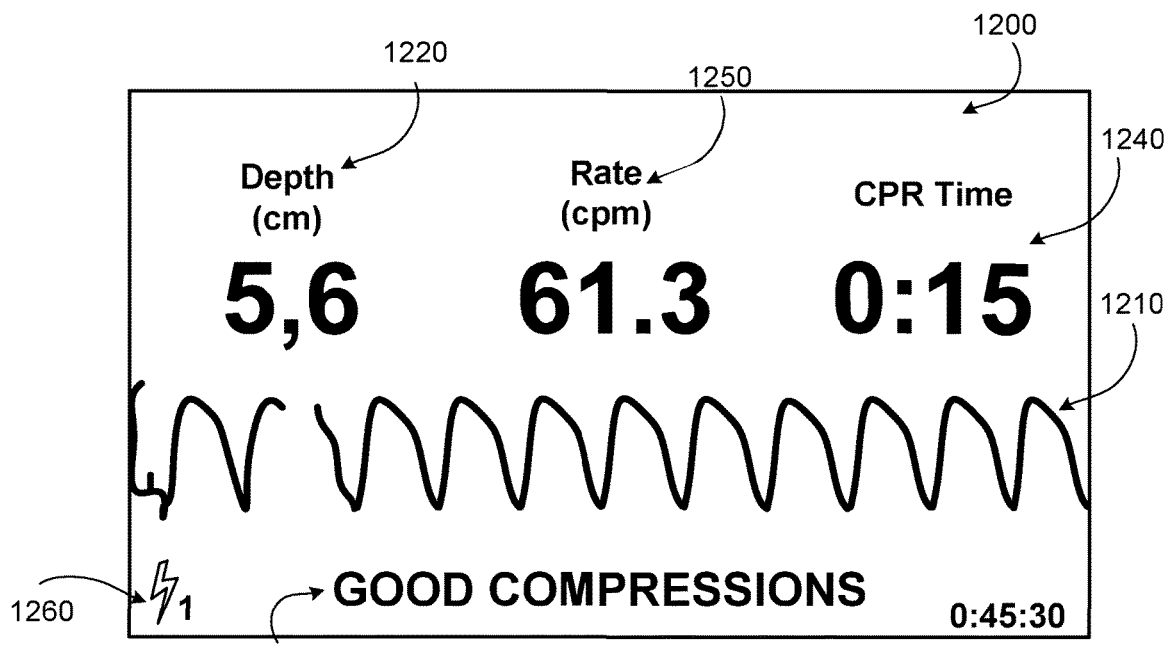

FIG. 12 shows an example of a professional adult CPR instruction 1200. In some examples, the instruction can be shown on the display 120 when the AED is configured to be in professional mode. In some examples, the professional mode can be called a basic life support mode, for personnel trained in basic life support protocols. The instruction can be intended for a more experienced user, such as a professional responder or those trained in advanced life support protocols. The instruction 1200 can be more complex and include more feedback than the corresponding instruction in a non-professional (e.g. lay person) mode, so that the professional is better able to assess the rescue performance. For example, an ECG scale marker 1210 measured by the AED can be displayed to the professional responder or user.

In some examples, numerical measurements of one or more of compression depth, rate, and time can be displayed. For example, a chest compression depth reading 1220 in centimeters can replace the compression feedback meter 730. Numerical readings could confuse or distract a non-professional and so can be reserved for professional users. Though, because professional users may often be trained based on numerical values for chest compression, it may be preferable for professional users to view actual numbers to determine the quality of chest compressions that are provided. In some implementations, a chest compression rate number 1250 and a CPR countdown timer 1240 can be displayed. A user prompt can be displayed. For example, a text 1230 reading "Good Compressions" can be displayed to the user when the user is giving proper compressions to the patient. A number of shocks delivered 1260 to the patient can be displayed.

The professional mode instructions can be distinguished from the non-professional instructions such that it is quickly apparent in which mode the AED is operating. In some examples, the professional mode instructions each have a black background. As with the non-professional instructions, professional instructions can include pictorial, textual, and auditory instructions and feedback. In some cases, the display or other portion of the device may provide an indicator for informing a user of the current operational mode of the device. For example, when in BLS mode, the display might show a textual or graphical representation of the operational mode, such as "BLS," or a checkbox that is marked or unmarked to indicate whether the device is set to BLS mode, or another ode.

As discussed above, depending on the mode of operation to which the device is set, the type of chest compression feedback may vary. For example, when the device is operating in BLS mode and adult operating mode, the display may show numerical values of depth and rate of chest compressions, and the device may further provide CPR feedback, such as prompts for the rescuer to adjust the manner in which chest compressions are applied, for example, by pushing harder, pushing deeper, pushing softer, pushing faster, pushing slower, fully releasing from the chest, amongst others. Though, when the device is operating is operating in BLS mode and pediatric operating mode, the display may show numerical values of depth and rate of chest compressions, however, in various embodiments, because the preferred ranges of CPR feedback for children can vary widely from person to person, no CPR feedback prompting is provided. Although, in some embodiments, even if the device is set in pediatric operating mode, it may be possible to provide an appropriate level of CPR feedback prompting. As further depicted, the professional mode display provides other information. For example, the display may show a CPR countdown timer indicating the amount of time remaining in the CPR interval; an indication of the amount of time that has elapsed since the start of rescue or when the device has been powered on; and the number of defibrillation shocks that have been provided to the patient during rescue. The display may also show the ECG rhythm of the patient. The ECG rhythm provided on the display may be a raw ECG rhythm as detected by the electrodes or, in some cases, the ECG rhythm shown on the display may be a processed ECG rhythm that accounts for and filters out artifacts due to chest compressions.

Figure 13:
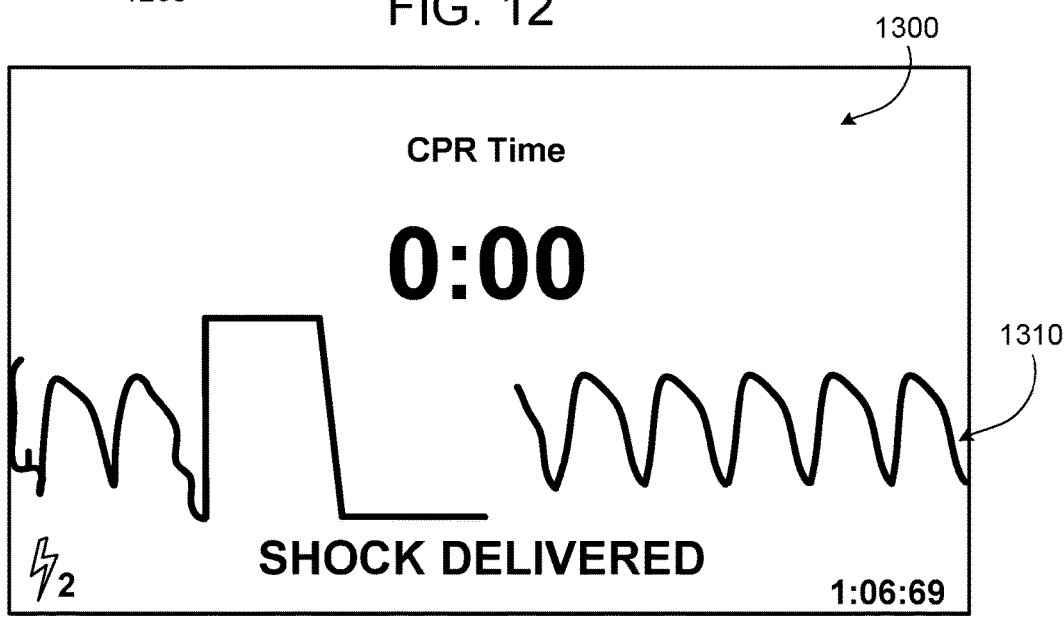

FIG. 13 is example of a display during a professional mode where shock therapy is delivered. As with FIG. 12, the instruction can be intended for a more experienced user, such as a professional responder. In some examples, the professional mode can be called a basic life support mode. The instructions provided in this mode can be more complex and include more feedback or information than the corresponding feedback or information provided in a non-professional (e.g. lay person) mode. For example, an ECG 1310 measured by the AED can be displayed to the professional responder or user. In some examples, in the basic life support mode, numerical measurements of one or more of compression depth, rate, and time can be displayed.

Figure 14:
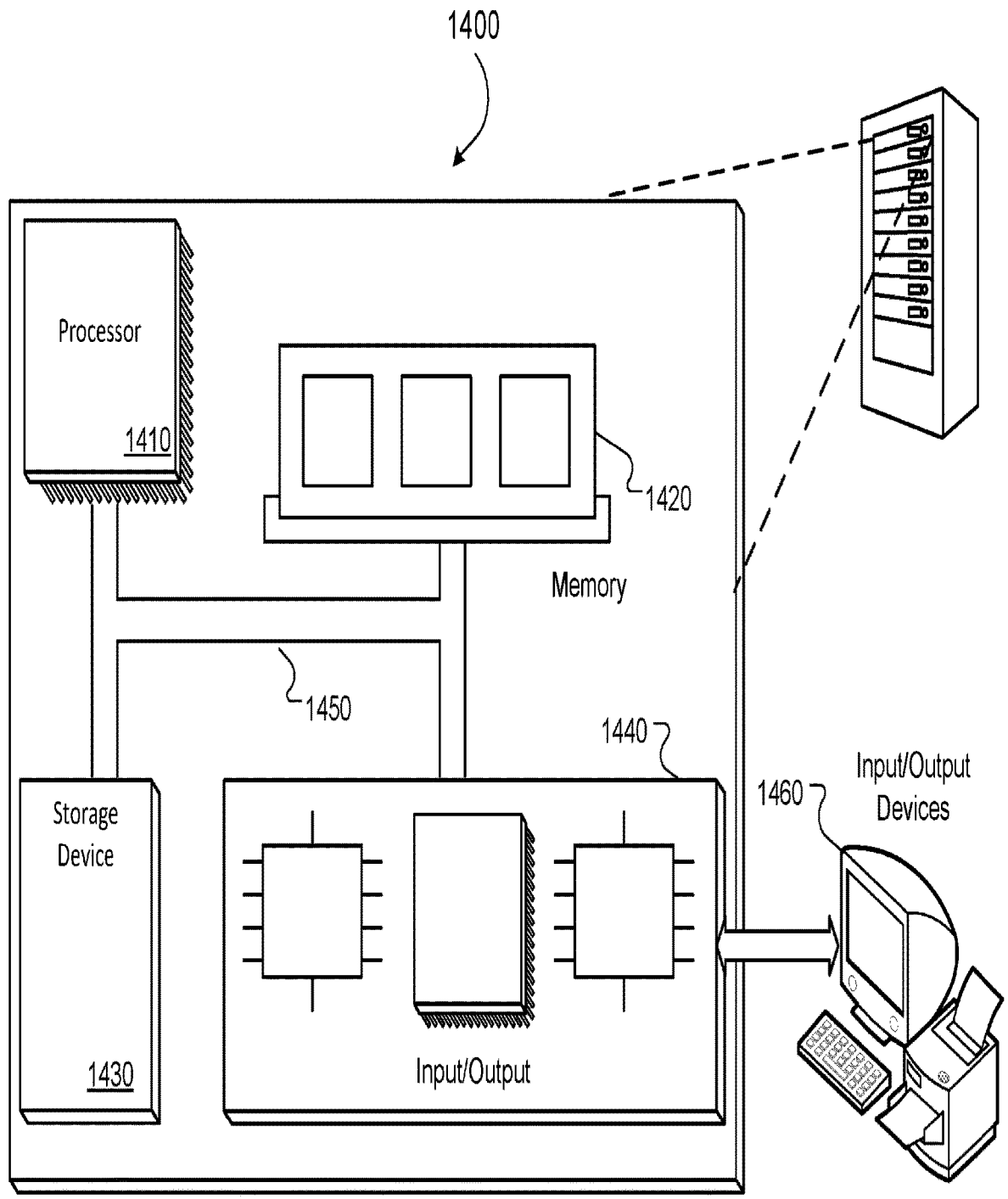
FIG. 14 is a block diagram of an example computer system.

FIG. 14 is a block diagram of an example computer system 1400. For example, referring to FIG. 1A, the AED is in the pediatric and/or adult setting. While in the professional mode, the device may also 100 could be an example of the system 1400 described here. The system 1400 includes a processor 1410, a memory 1420, a storage device 1430, and one or more input/output interface devices 1440. Each of the components 1410, 1420, 1430, and 1440 can be interconnected, for example, using a system bus 1450.

The processor 1410 is capable of processing instructions for execution within the system 1400. The term "execution" as used here refers to a technique in which program code causes a processor to carry out one or more processor instructions. In some implementations, the processor 1410 is a single-threaded processor. In some implementations, the processor 1410 is a multi-threaded processor. In some implementations, the processor 1410 is a quantum computer. The processor 1410 is capable of processing instructions stored in the memory 1420 or on the storage device 1430. The processor 1410 may execute operations such as reading input data, determining levels of electric shock therapy, and other functions described in more detail above.

The memory 1420 stores information within the system 1400. In some implementations, the memory 1420 is a computer-readable medium. In some implementations, the memory 1420 is a volatile memory unit. In some implementations, the memory 1420 is a non-volatile memory unit.

The storage device 1430 is capable of providing mass storage for the system 1400. In some implementations, the storage device 1430 is a non-transitory computer-readable medium. In various different implementations, the storage device 1430 can include, for example, a hard disk device, an idle timeroptical disk device, a solid-state drive, a flash drive, magnetic tape, or some other large capacity storage device. In some examples, the storage device may store long-term data, such as ECG readings, chest compression information, or other data as shown in FIG. 1A. The input/output interface devices 1440 provide input/output operations for the system 1400. In some implementations, the input/output interface devices 1440 can include one or more of a network interface devices, e.g., an Ethernet interface, a serial communication device, e.g., an RS-232 interface, and/or a wireless interface device, e.g., an 802.11 interface, a 3G wireless modem, a 4G wireless modem, etc.

In some implementations, the input/output device can include driver devices configured to receive input data and send output data to other input/output devices, e.g., keyboard, printer and display devices 1460. In some implementations, mobile computing devices, mobile communication devices, and other devices can be used.

Referring to FIG. 1A, operation of the AED can be realized by instructions that upon execution cause one or more processing devices to carry out the processes and functions described above, for example, treating the adult or pediatric patient. Such instructions can include, for example, interpreted instructions such as script instructions, or executable code, or other instructions stored in a computer readable medium.

In some examples, the system 1400 is contained within a single integrated circuit package. A system 1400 of this kind, in which both a processor 1410 and one or more other components are contained within a single integrated circuit package and/or fabricated as a single integrated circuit, is sometimes called a microcontroller. In some implementations, the integrated circuit package includes pins that correspond to input/output ports, e.g., that can be used to communicate signals to and from one or more of the input/output interface devices 1440.

Although an example processing system has been described in FIG. 14, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that appears when chest compressions have prematurely ceased. The idle timer may provide the user with an indication of the time elapsed since CPR chest compressions have stopped, socreates an execution environment for the computer program in question, e.g., code that the rescuer may know whether an appreciable amount of time have elapsed without chest compressions. Accordingly, the rescuer may be more encouraged to apply chest compressions to the patient as the idle timer continues to appear and/or display long idle times. constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry.

What is claimed is:

1. A system for providing external defibrillation to adult and pediatric patients, comprising:
an automated external defibrillator (AED) comprising:
one or more capacitors for delivering a defibrillating shock to a patient;
one or more electronic ports configured to receive signals indicative of one or more sensed physiological parameters of the patient and to communicate the defibrillating shock to the patient;
a button configured to, upon being pressed, toggle between a pediatric operating mode and an adult operating mode during a resuscitation process, wherein each of the pediatric operating mode and the adult operating mode comprises a different mode-specific energy configuration;
one or more processors configured to switch the mode-specific energy configuration upon a change between the pediatric operating mode and the adult operating mode, wherein, in the pediatric operating mode, the AED is configured to deliver the defibrillating shock at a lower energy level than in the adult operating mode;
a user interface configured to:
upon a change from the adult operating mode to the pediatric operating mode, present an auditory announcement of the change from the adult operating mode to the pediatric operating mode, and
provide mode-specific treatment related guidance, comprising mode-specific chest compression related guidance, such that, when the AED is in the adult operating mode, the mode-specific treatment related guidance is suitable for treatment of an adult patient, and, when the AED is in the pediatric operating mode, the mode-specific treatment related guidance is suitable for treatment of a pediatric patient; and
an interface device configured to wirelessly transmit data to a device other than the AED.

2. The system of claim 1, wherein the user interface is configured to, upon a change from the pediatric operating mode to the adult operating mode, present a second auditory announcement of the change from the pediatric operating mode to the adult operating mode.

3. The system of claim 1, wherein the user interface is configured to, upon the change from the adult operating mode to the pediatric operating mode, present a visual indication of the change from the adult operating mode to the pediatric operating mode.

4. The system of claim 3, wherein the user interface is configured to, upon the change from the adult operating mode to the pediatric operating mode, provide the visual indication by illuminating an indicator.

5. The system of claim 4, wherein the indicator is not illuminated when the AED is in the adult operating mode.

6. The system of claim 3, wherein the one or more electronic ports are configured to be attached to at least one electrode assembly.

7. The system of claim 3, wherein system provides instructions for placement of at least a piece of the at least one electrode assembly on a chest of an adult patient.

8. The system of claim 3, wherein the system provides instructions for placement of at least a piece of the at least one electrode assembly on a back of a pediatric patient.

9. The system of claim 1, wherein the interface device is configured to wirelessly transmit the data to the device other than the AED, wherein the device is a display device.

10. The system of claim 1, wherein the interface device is configured to wirelessly transmit the data for display.

11. The system of claim 1, wherein the interface device is configured to wirelessly transmit the data to the device other than the AED, wherein the device is a mobile computing device.

12. The system of claim 1, wherein the interface device is configured to wirelessly transmit the data to the device other than the AED, wherein the device is a mobile communication device.

13. The system of claim 1, wherein the auditory announcement comprises audible words.

14. The system of claim 1, wherein the auditory announcement comprises audible words comprising words identifying the pediatric operating mode.

15. The system of claim 1, wherein, in the pediatric operating mode, the AED is configured to deliver the defibrillating shock of between 50 and 85 Joules.

16. The system of claim 1, wherein, in the pediatric operating mode, the AED is configured to deliver the defibrillating shock of between 50 and 75 Joules.

17. The system of claim 1, wherein, in the pediatric operating mode, the AED is configured to deliver the defibrillating shock of 50 Joules.

18. The system of claim 1, wherein, in the pediatric operating mode, the AED is configured to deliver the defibrillating shock of 75 Joules.

19. The system of claim 15, wherein, in the adult operating mode, the AED is configured to deliver the defibrillating shock of between 120 and 200 Joules.

20. The system of claim 15, wherein, in the adult operating mode, the AED is configured to deliver the defibrillating shock of between 150 and 200 Joules.

21. The system of claim 15, wherein, in the adult operating mode, the AED is configured to deliver the defibrillating shock of between 175 and 200 Joules.

22. The system of claim 15, wherein, in the adult operating mode, the AED is configured to deliver the defibrillating shock of between 200 Joules.

23. The system of claim 1, wherein the guidance comprises chest compression feedback.

24. The system of claim 1, wherein the guidance comprises CPR feedback.

25. The system of claim 1, wherein the guidance comprises visual guidance.

26. The system of claim 1, wherein the guidance comprises textual guidance.

27. The system of claim 1, wherein the guidance comprises haptic guidance.

28. The system of claim 1, wherein the guidance comprises auditory guidance.

29. The system of claim 1, wherein the guidance comprises a metronome tone for providing guidance relating to performing chest compressions.

30. The system of claim 1, wherein the AED is configured to deliver the defibrillating shock of 200 Joules to the patient when the patient has a patient impedance of between 25 and 125 ohms.

31. The system of claim 1, wherein the AED comprises a readiness indicator configured to provide an indication of whether the AED is ready for use.

32. The system of claim 1, wherein the AED is configured to perform a self-test to determine whether the AED is ready for the use.

33. The system of claim 1, wherein the one or more processors are configured to perform a mode-specific analysis of the one or more sensed physiological parameters in determining whether the defibrillating shock should be administered to the patient, such that, when the AED is in the pediatric operating mode, the mode-specific analysis is suitable for the pediatric patient and, when the AED is in the adult operating mode, the mode-specific analysis is suitable for the adult patient.

34. The system of claim 33, wherein the one or more processors are configured to perform the mode-specific analysis of the one or more sensed physiological parameters in determining whether the defibrillating shock should be administered to the patient, wherein the sensed one or more physiological parameters comprise an ECG signal.

35. The system of claim 1, wherein the AED comprises an indicator, visually associated with the button, configured to, when the pediatric operating mode is in use, provide a visual indication that the pediatric operating mode is in use.

* * * * *